(12) United States Patent
Annapragada et al.

(10) Patent No.: US 8,679,531 B2
(45) Date of Patent: Mar. 25, 2014

(54) VESICLE COMPOSITIONS

(76) Inventors: Ananth Annapragada, Manvel, TX (US); Indrani Dasgupta, Frederick, MD (US); Eric Tanifum, Katy, TX (US); Mayank Srivastava, Pearland, TX (US); Mostafa Analoui, Madison, CT (US)

( * ) Notice: Subject to any disclaimer, the term of this patent is extended or adjusted under 35 U.S.C. 154(b) by 0 days.

(21) Appl. No.: 13/411,415

(22) Filed: Mar. 2, 2012

(65) Prior Publication Data
US 2012/0231067 A1    Sep. 13, 2012

Related U.S. Application Data

(60) Provisional application No. 61/448,556, filed on Mar. 2, 2011.

(51) Int. Cl.
*A61K 9/127* (2006.01)
*A61K 38/28* (2006.01)
*A61P 3/10* (2006.01)

(52) U.S. Cl.
USPC ............................................ 424/450; 514/59

(58) Field of Classification Search
USPC ....................................................... 424/450
See application file for complete search history.

(56) References Cited

U.S. PATENT DOCUMENTS

| 5,631,018 A * | 5/1997 | Zalipsky et al. ............... 424/450 |
| 2004/0062746 A1 | 4/2004 | Martinez et al. |
| 2007/0148255 A1 * | 6/2007 | Tardi et al. ..................... 424/490 |
| 2010/0029545 A1 | 2/2010 | Sumerlin et al. |
| 2010/0040556 A1 * | 2/2010 | Davis et al. ................... 424/9.37 |

OTHER PUBLICATIONS

Karathanasis E, Glucose sensing pulmonary delivery of human insulin to the systemic circulation of rats, 2007, Dove medical press, Intl J Nanomed, 2(3), 501-513.*
Hirota, et al., "Physicochemical Specification of Drug Carrying Liposomes for the Quality Control in the Industrial Production," International Journal of Pharmaceutics, 1998, 162, 185-194.
Wang, et al., "Glucose-responsive Micelles From Self-Assembly of Poly(ethylene glycol)-b-poly(acrylic acid-co-acrylamidophenylboronic acid) and the Controlled Release of Insulin," Langmuir, 2009, 25, 12522-8.
International Search Report issued Jun. 1, 2012 in corresponding PCT application Ser. No. PCT/US2012/27579.

* cited by examiner

*Primary Examiner* — Frederick Krass
*Assistant Examiner* — Celeste A Roney
(74) *Attorney, Agent, or Firm* — Benjamen E. Kern

(57) ABSTRACT

Vesicle compositions are provided that comprise a therapeutic compound. The vesicle compositions may be capable of releasing the therapeutic compound in response to the presence of an external trigger. The vesicle compositions may comprise a plurality of biocompatible vesicles. The biocompatible vesicles may comprise a therapeutic compound for treatment of a patient in need thereof, and one or more cross-linkages between two or more of the biocompatible vesicles, each cross-linkage comprising a chemical sensing moiety and a sensed moiety. In some embodiments, the therapeutic compound may be any compound that provides palliative, curative, or otherwise beneficial effects to a patent.

17 Claims, 20 Drawing Sheets

| Boronic Acid | Structure | Glucose Binding Affinity | % Cell Survival (80nM) | PCC (80nM) |
|---|---|---|---|---|
| 4-aminocarboxyphenyl boronic acid | | 45 M$^{-1}$ | 97% | 0.01 |
| 3-N,N-dimethylamino phenyl boronic acid | 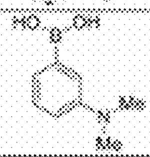 | 357 M$^{-1}$ | 86% | -0.04 |
| 3-chlorophenyl boronic acid | 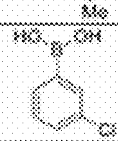 | 46 M$^{-1}$ | 73% | 0.03 |
| 2,4-dichlorophenyl boronic acid | 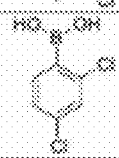 | 58 M$^{-1}$ | 81% | 0.09 |
| 4-hydroxyphenyl boronic acid | 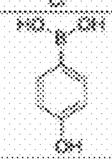 | 80 M$^{-1}$ | 108% | -0.01 |
| 2,4-ditertbutoxypyrimidin-5-yl-boronic acid | 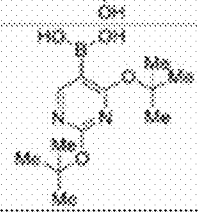 | 608 M$^{-1}$ | 90% | 0.03 |

Figure 8

VESICLE COMPOSITIONS

CROSS-REFERENCE TO RELATED APPLICATIONS

This application claims priority from U.S. Provisional Patent Application No. 61/448,556, filed on Mar. 2, 2011, which is incorporated by reference herein in its entirety.

STATEMENT REGARDING FEDERALLY SPONSORED RESEARCH OR DEVELOPMENT

This invention was made with Government support under R43 DK083819 awarded by the National Institute of Health. The Government has certain rights in the invention.

BACKGROUND

Diabetes is a disease caused by an insulin deficiency or a resistance to insulin in the body. Type I diabetes is an autoimmune disease that damages the beta cells of the islets of Langerhans in the pancreas, resulting in an inadequate amount of insulin in the body. Without insulin treatments, Type I diabetes is fatal. Type II diabetes results from an insufficient production of insulin or an inability of the patient's body to respond properly to insulin. Insulin resistance associated with Type II diabetes prevents adequate levels of blood sugar from entering into cells to be stored for energy, resulting in hyperglycemia in the bloodstream. Traditionally, Type I diabetes is treated by repeated subcutaneous injections of insulin each day. Type II diabetes is also treated with insulin, often in combination with other medications taken orally or by injection. Multiple injections of insulin per day are required, as well as careful monitoring of the patient's blood glucose levels through dietary control and blood testing. Insulin pumps are used as an alternative to multiple daily insulin injections by a syringe. However, insulin pumps are costly, must be worn most of the time, and require blood testing to determine the amount of insulin to deliver into the patient. Blood testing requires the patient to draw a sample of blood, usually from a finger, and to test the blood sample for glucose concentration. Blood glucose monitoring systems are available that use a sensor placed just under the skin to periodically monitor the amount of glucose in the interstitial fluid. These systems require calibration, typically resulting in two finger pricks per day, and are costly. Moreover, a lag time exists between the concentration of glucose in the bloodstream and the concentration of glucose in the interstitial fluid.

A need exists for a system or device that delivers controlled amounts of insulin directly in response to increased glucose concentrations, without requiring the patient or medical professional to continuously monitor the blood glucose level, determine the appropriate amount of insulin to be injected, and inject the insulin periodically throughout the day.

SUMMARY

Vesicle compositions are provided that comprise a therapeutic compound. The vesicle compositions may be capable of releasing the therapeutic compound in response to the presence of an external trigger. The vesicle compositions may comprise a plurality of biocompatible vesicles. The biocompatible vesicles may comprise a therapeutic compound for treatment of a patient in need thereof, and one or more cross-linkages between two or more of the biocompatible vesicles, each cross-linkage comprising a chemical sensing moiety and a sensed moiety. In some embodiments, the therapeutic compound may be any compound that provides palliative, curative, or otherwise beneficial effects to a patent. The vesicle compositions may be suitable for injection into a patient.

Vesicle compositions are also provided that comprise a plurality of biocompatible vesicles, the biocompatible vesicles comprising a therapeutic compound for treatment of a patient in need thereof, and one or more cross-linkages between two or more of the biocompatible vesicles, each cross-linkage comprising a boronic acid moiety or a boronic acid derivative moiety and a sugar moiety.

Further, methods are provided for administering a therapeutic compound to a patient in need thereof. These methods may comprise injecting a vesicle composition parenterally into a patient in need of treatment, the vesicle composition comprising a therapeutic compound; and releasing the therapeutic compound into the patient in response to a triggering event.

Methods are also provided for treating a medical condition, the methods comprising administering a vesicle composition into a patient in need of treatment, wherein the vesicle composition is loaded with a therapeutic compound for treatment of a patient in need thereof; and releasing the therapeutic compound into the patient in response to a triggering event.

The general description and the following detailed description are exemplary and explanatory only, and are not intended to be restrictive of the invention, as defined in the claims. Other embodiments will become apparent to those skilled in the art, in view of the detailed description provided herein.

BRIEF DESCRIPTION OF THE DRAWINGS

In the accompanying figures, chemical formulas, chemical structures, and experimental data are given that, together with the detailed description provided below, describe example embodiments of the claimed invention.

FIG. 8 shows the structure, glucose binding affinity, percent HeLa cell survival at 80 nM, and the PCC between the nuclear and cytoplasmic fractions of the NF-κB molecule in HeLa cells at 80 nM, of various boronic acid derivatives.

DETAILED DESCRIPTION

The present invention may be understood more readily by reference to the following detailed description taken in connection with the accompanying figures and examples, which form a part of this disclosure. This invention is not limited to the specific devices, methods, applications, conditions, or parameters described and/or shown herein. The terminology used herein is for the purpose of describing particular embodiments by way of example only, and is not intended to be limiting. As used in the specification and the claims, the singular forms "a," "an," and "the" include the plural. The term "plurality," however, means more than one. Reference to a particular numerical value includes at least that particular value, unless the context clearly dictates otherwise. When a range of values is expressed, another embodiment includes from the one particular value and/or to the other particular value. The particular value forms another embodiment. Where the term "about" is used in conjunction with a number, it is intended to include ±10% of the number. For example, "about 10" may mean from 9 to 11.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use.

Certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination.

Figure 1:
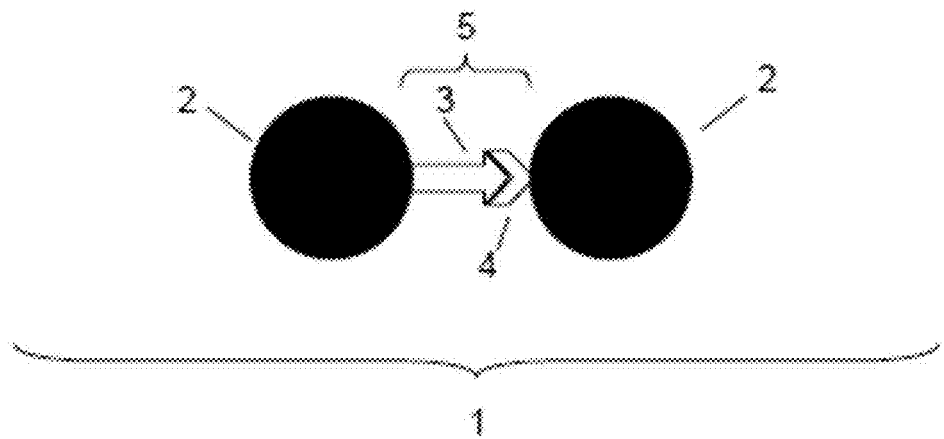
FIG. 1 illustrates one embodiment of a vesicle composition.
Figure 2:
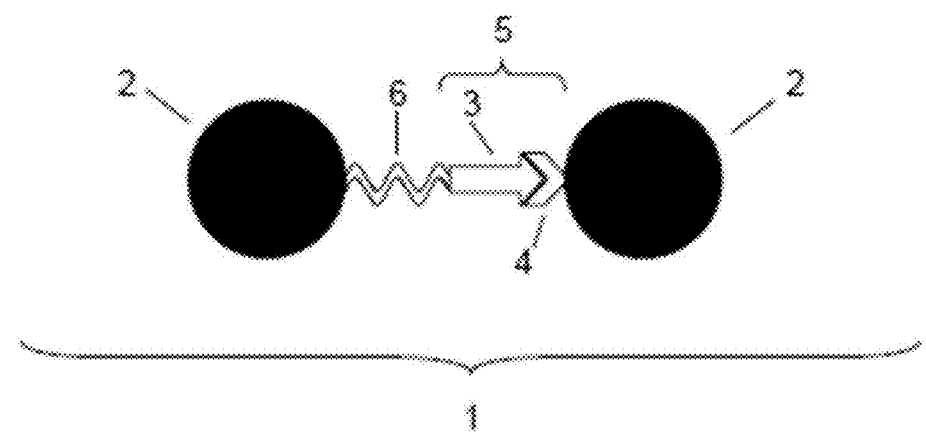
FIG. 2 illustrates one embodiment of a vesicle composition.
Figure 3:
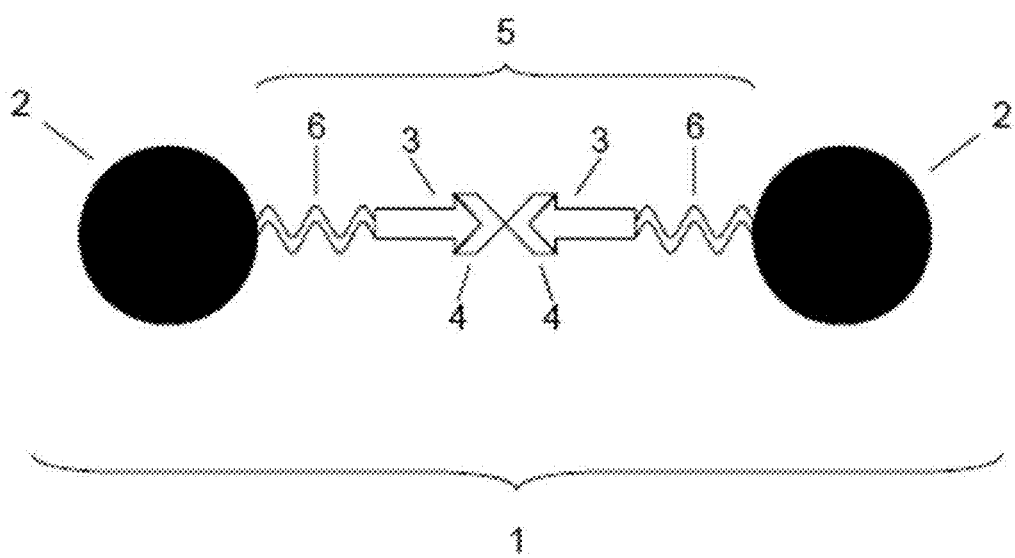
FIG. 3 illustrates one embodiment of a vesicle composition.

The present invention may be more readily understood by reference to FIGS. 1, 2, and 3. In FIG. 1, a schematic of one embodiment of a vesicle composition 1 is shown. As shown in FIG. 1, vesicle composition 1 comprises a plurality of biocompatible vesicles 2. In one embodiment, the plurality of biocompatible vesicles 2 may be, for example, non-toxic and biodegradable. As shown in FIG. 1, vesicle composition 1 further comprises one or more chemical sensing moieties 3. In one embodiment, the one or more chemical sensing moieties 3 may be, for example, one or more chemical moieties that are capable of reversibly bonding with a conjugate moiety. As shown in FIG. 1, vesicle composition 1 further comprises one or more sensed moieties 4. In one embodiment, the one or more sensed moieties 4 may be, for example, chemical moieties that are capable of reversibly bonding with a chemical sensing moiety, e.g., 3. As used herein, the phrase "sensed moiety" may encompass both bound sensed moieties that are attached to a biocompatible vesicle (as shown in FIG. 1), and free sensed moieties that are sensed moieties not bound to a biocompatible vesicle but are present in the physiological environment (i.e., the environment within the body of a patient). Returning to FIG. 1, a first biocompatible vesicle 2 is attached to a chemical sensing moiety 3, while a second biocompatible vesicle 2 is attached to a sensed moiety 4. Chemical sensing moiety 3 and sensed moiety 4, when attached together, form crosslink 5.

FIG. 2 illustrates another embodiment of a vesicle composition 1. A first biocompatible vesicle 2 is attached to a polymer linker 6, and the polymer linker 6 is attached to a chemical sensing moiety 3. A second biocompatible vesicle 2 is attached to a sensed moiety 4. The chemical sensing moiety 3 and sensed moiety 4, when attached together, form crosslink 5.

FIG. 3 illustrates still another embodiment of a vesicle composition 1. A biocompatible vesicle 2 is attached to a first polymer linker 6, and the first polymer linker 6 is attached to a first chemical sensing moiety 3. A second biocompatible vesicle 2 is attached to a second polymer linker 6, and the second polymer linker 6 is attached to a second chemical sensing moiety 3. Two sensed moieties 4 are attached together and each chemical sensing moiety 3 is attached to a sensed moiety 4. The chemical sensing moieties 3 and sensed moieties 4, when attached together, form a crosslink 5.

A biocompatible vesicle may be any biocompatible particle capable of carrying a therapeutic compound. The biocompatible vesicle may be approximately spherical in shape with an inner portion. The therapeutic compound can be carried in the inner portion of the vesicle, in the wall of the vesicle, attached to the outer surface of the vesicle, or by any other suitable means. The biocompatible vesicle may comprise polymers, lipids, proteins, carbohydrates, other macromolecules, waters, and salts, or any combination thereof. For example, the biocompatible vesicle may comprise a liposome comprised of a plurality of lipids. The lipids may comprise saturated lipids. In one embodiment, the biocompatible vesicle may be comprised of distearoylphosphatidylethanolamine (DSPE), dipalmitoylphosphatidylethanolamine (DPPE), dipalmitoylphosphatidylcholine (DPPC), distearoylphosphatidylcholine (DSPC), or any combination thereof. The biocompatible vesicle may have a sufficient shelf life to be suitable as a delivery system for a therapeutic compound. In one embodiment, the biocompatible vesicle may have a shelf life stability of at least six months at from about 2° C. to about 8° C., or a shelf life stability of at least seven days at room temperature.

Suitable vesicle compositions may include a therapeutic compound. In one embodiment, the therapeutic compound may be loaded in or on the biocompatible vesicles. In one embodiment, the vesicle composition may be capable of releasing the therapeutic compound into the physiological environment of a patient. The physiological environment of the patient is ordinarily the bloodstream, but may be any environment within the patient's body into which the vesicle composition is delivered. In one embodiment, the therapeutic compound will be released from the vesicle composition in response to the presence of a free sensed moiety in the physiological environment. In one embodiment, the free sensed moiety in the physiological environment that triggers release of the therapeutic compound is symptomatic of the condition sought to be treated by the therapeutic compound. In formulations where the vesicle is suitable for injection into a patient, the weight percentage of the therapeutic compound based on the total weight of the vesicle composition may be in the range of from about 0.1% to about 30%, or from about 0.2% to about 20%, or from about 1% to about 10%. The therapeutic compound may be any compound administered to a patient to provide palliative, curative, or otherwise beneficial effects. Example therapeutic compounds may include insulin and ciprofloxacin. In some embodiments where the therapeutic compound is insulin, the insulin may be present in a concentration in the range of from 0.1 mg/mL to 10 mg/mL, or from about 0.5 mg/mL to about 5 mg/mL, or from about 1 mg/mL to 3 mg/mL, such as 2 mg/mL.

In some embodiments, the quantity of therapeutic compound released is related to the quantity of sensed moiety present in the physiological environment of the patient. For example, the quantity of therapeutic compound released and the quantity of sensed moiety in the environment may be linearly proportional or may be related by a non-linear function. Accordingly, an increase in the concentration of free sensed moiety in the physiological environment may trigger an increase in the amount of therapeutic compound released from the vesicle composition. For example, the vesicle composition may release the therapeutic compound insulin in response to the presence of free sensed moieties that are sugars in the physiological environment. When the concentration of sugar free sensed moieties increases, the concentration of insulin released may also increase. Example sugars may include glucose, galactose, maltose, lactose, fructose, sucrose, or any combination thereof. In one embodiment, the release of insulin may be triggered by the presence of glucose in the physiological environment. In alternative embodiments, sugars may be used to trigger the release of therapeutic compounds other than insulin.

In some embodiments, the chemical sensing moiety may be attached directly to the biocompatible vesicle. A linker moiety can be positioned between the chemical sensing moiety and the biocompatible vesicle. In embodiments where the biocompatible vesicle is a liposome, the linker moiety may be attached to a lipid that is part of the liposome. The linker moiety may be a biodegradable polymer moiety, such as, for example, polyethylene glycol (PEG). The linker moiety may provide flexibility between the biocompatible vesicle and the chemical sensing moiety. One way of characterizing the flexibility of the linker moiety is the density of unsaturated bonds in each repeating unit of the polymer moiety. In one embodiment, each repeating unit of the polymer comprising the linker moiety may contain at least one unsaturated bond. Another way of characterizing the flexibility of the linker moiety is by its length. Where the linker moiety is PEG, each PEG moiety independently may have a molecular weight in the range of from about 100 to about 10,000 Da, such as, for example, in the range of from about 500 to about 5,000 Da. In one embodiment, the PEG linker moiety comprises about 10-100 ethylene glycol repeating units. In another embodiment, the PEG linker moiety comprises about 30-60 ethylene glycol repeating units.

The sensed moiety may be capable of being attached, such as by a covalent bond, to the chemical sensing moiety. The sensed moiety may be a bound sensed moiety that is attached to a biocompatible vesicle, which, together with a chemical sensing moiety, forms a crosslink in the vesicle composition. Alternatively, the sensed moiety may be a free sensed moiety, which competes with bound sensed moieties to bond with a chemical sensing moiety. In one embodiment, the free sensed moiety in the physiological environment may serve as a trigger to release therapeutic compound by competitively bonding with a chemical sensing moiety and thereby cleaving crosslinks between biocompatible vesicles.

The sensed moiety may be related to the disease or condition sought to be treated by the therapeutic compound. For example, in some embodiments where the condition sought to be treated by the therapeutic compound is diabetes or another metabolic disorder that results in hyperglycemia, the free sensed moiety that triggers release of the therapeutic compound is a sugar. Example sugars may include glucose, galactose, maltose, lactose, fructose, sucrose, or any combination thereof. In one embodiment, the sugar is glucose. In embodiments where the condition to be treated is diabetes or another metabolic disorder that results in hyperglycemia and the free sensed moiety is a sugar, the therapeutic compound may be insulin. In some embodiments where the condition sought to be treated is inflammation, the chemical compound that triggers the release of the therapeutic compound may be nitric oxide. In some embodiments, amyloid beta 42 may trigger the release of a therapeutic compound to treat potential plaque formation. In other embodiments, albumin, alkaline phosphatase, alanine transaminase (ALT), aspartate aminotransferase (AST), blood urea nitrogen (BUN), calcium, chloride, carbon dioxide, creatinine, direct bilirubin, gamma-glutamyl transpeptidase (Gamma-GT), glucose, lactate dehydrogenase (LDH), phosphorus, potassium, sodium, total bilirubin, total cholesterol, total protein, uric acid, or any combination thereof may act as a free sensed moiety.

The chemical sensing moiety and the sensed moiety are chemical groups that may be capable of reversibly attaching to each other. The attachment may be a chemical bond, such as a covalent bond. The covalent bond between the chemical sensing moiety and the sensed moiety may be capable of cleaving in the presence of competing free sensed moieties in the environment. When the vesicle composition has been delivered into a patient, the covalent bond between the chemical sensing moiety and the sensed moiety may be capable of cleaving in the presence of free sensed moieties in the physiological environment. Where different chemical sensing moieties are attached to each biocompatible vesicle, the crosslinkages formed by the different chemical sensing moieties and the sensed moieties may have different strengths. The degree of cleavage of crosslinks and the rate of release of the therapeutic compound may depend on the number of strong, weak, and moderate crosslinkages present.

Suitable chemical sensing moieties may include a boronic acid or a boronic acid derivative. Example boronic acid derivatives may include phenylboronates, pyridylboronates, and cyclohexylboronates. In one embodiment, the boronic acid derivative may be 3-(N,N-dimethylamino)phenyl boronic acid; 2,4-dichlorophenylboronic acid; 4-aminocarbonylphenylboronic acid; 3-chlorophenylboronic acid; 4-hydroxyphenylboronic acid; 4-propylphenylboronic acid; 3-[(E)-2-nitrovinyl]phenylboronic acid; 4-chlorocarbonylphenylboronic anhydride; cyclopenten-1-ylboronic acid; 2-bromopyridine-3-boronic acid; 2,4-ditert-butoxypyrimidin-5-ylboronic acid; 2,4-bis(benzyloxy)pyrimidine-5-boronic acid; 5-phenyl-2-thienylboronic acid; 5-formylthiophene-3-boronic acid; or any combination thereof.

The sensed moiety may be a sugar in embodiments in which the chemical sensing moiety is a boronic acid or a boronic acid derivative. Suitable sugars may include glucose, galactose, maltose, lactose, fructose, sucrose, or any combination thereof. In one embodiment, the sensed moiety may be glucose where the chemical sensing moiety is boronic acid or a boronic acid derivative. In some embodiments, each biocompatible vesicle may have only one kind of boronic acid or boronic acid derivative attached to it. In other embodiments, each biocompatible vesicle may have either one kind of boronic acid or boronic acid derivative attached to it or more than one kind of boronic acid attached to its surface. Where different boronic acid derivatives are attached to each biocompatible vesicle, the crosslinkages formed by the different boronic acid derivatives may have different strengths. The degree of cleavage of crosslinks and the rate of release of the therapeutic compound may depend on the number of strong, weak, and moderate crosslinkages present.

The biocompatible vesicles, chemical sensing moieties, sensed moieties, and crosslinks forming the vesicle composition may be arranged in any number of ways. The biocompatible vesicles may each have multiple moieties attached, the moieties being chemical sensing moieties, sensed moieties, or both. Alternatively, the biochemical vesicles each may have only one moiety attached, either a chemical sensing moiety or a sensed moiety. Also, the biocompatible vesicles each may have any number of moieties attached with some biocompatible vesicles having one moiety attached and other biocompatible vesicles having more than one moiety attached. In some embodiments, the biocompatible vesicles may have both chemical sensing moieties and sensed moieties attached to the same biocompatible vesicle. In one embodiment, the biocompatible vesicles each have only chemical sensing moieties or only sensed moieties attached. Suitable vesicle compositions may be comprised of as few as two biocompatible vesicles. Suitable vesicle compositions may also comprise between about 10 and about $10^8$ biocompatible vesicles. In one embodiment, the vesicle composition may comprise between about $10^2$ and about $10^7$ biocompatible vesicles. In one embodiment, the vesicle composition may comprise between about $10^3$ and about $10^7$ biocompatible vesicles. The moieties attached to the biocompatible vesicles may be arranged in any geometry that will allow crosslinks to be formed and cleaved between chemical sensing moieties and sensed moieties. The chemical sensing or sensed moieties may be arranged on the biocompatible vesicle in any geometry. In some embodiments, the moieties will be equally spaced about the biocompatible vesicle. In other embodiments, moieties will be attached to the biocompatible vesicle in a random fashion. Regardless of the geometry of the biocompatible particles, attached moieties, and crosslinks which they form, the vesicle composition may assume a folded or otherwise agglomerated geometry. In some embodiments, the vesicle composition may have a diameter in the range of from about 0.1 micrometers to about 50 micrometers. In one embodiment, the vesicle composition may have a diameter in the range of from about 0.5 micrometers to about 30 micrometers. In one embodiment, the vesicle composition may have a diameter in the range of from about 1 micrometer to about 20 micrometers.

The vesicle composition may be suitable for injection into a patient. One method for measuring suitability for injection is to test for the degree of inflammation caused by a PEG-lipid composition comprising the chemical sensing moiety. One measure for the degree of inflammation is an NF-κβ protein assay. In one embodiment, the PEG-lipid composition comprising the chemical sensing moiety tested using an NF-κβ assay results in a PCC of less than about 0.2. In one embodiment, when the concentration of the PEG-lipid composition comprising the chemical sensing moiety is in the range of from about 40 nM to 160 nM, e.g., about 80 nM, the PCC between the nuclear and cytoplasmic fraction of the NF-κβ molecule is less than about 0.2, e.g., less than about 0.1. In one embodiment, the PEG-lipid composition comprising the chemical-sensing moiety may be capable of causing less inflammation than the chemical sensing moiety single molecule, as measured by an NF-κβ translocation assay.

Another method for measuring the suitability for injection of the vesicle composition is to measure the cell toxicity of the chemical sensing moiety. The vesicle composition is suitable for injection if the chemical sensing moiety is characterized as giving rise to greater than about 82% cell survival as measured according to an MTT cell proliferation assay. The chemical sensing moiety may be characterized as giving rise to greater than 82% cell survival as measured according to an MTT cell proliferation assay, when the chemical sensing moiety is dosed at a concentration in the range of from about 40 nM to about 160 nM.

In another embodiment, a method is provided for administering a therapeutic compound to a patient in need thereof, the method comprising injecting a vesicle composition parenterally into the patient, the vesicle composition including a therapeutic compound, and releasing the therapeutic compound into the patient in response to a triggering event. The vesicle composition may be comprised of a therapeutic compound, biocompatible vesicles, one or more chemical sensing moieties, one or more sensed moieties, and crosslinks between the chemical sensing and sensed moieties. In one embodiment, the triggering event is symptomatic of the condition sought to be treated by the therapeutic compound. In one embodiment, the triggering event may be the presence of free sensed moiety in the physiological environment. In some embodiments, an increase in concentration of free sensed moiety in the physiological environment may result in release of therapeutic compound.

In one embodiment, the method may comprises administering a vesicle composition where the chemical sensor is a boronic acid or boronic acid derivative, the sensed moiety is a sugar, and the therapeutic compound is insulin. In one embodiment, boronic acid derivatives may include phenylboronates, pyridylboronates, and cyclohexylboronates. In one embodiment, the boronic acid derivative may be 3-(N,N-dimethylamino)phenyl boronic acid; 2,4-dichlorophenylboronic acid; 4-aminocarbonylphenylboronic acid; 3-chlorophenylboronic acid; 4-hydroxyphenylboronic acid; 4-propylphenylboronic acid; 3-[(E)-2-nitrovinyl)phenylboronic acid; 4-chlorocarbonylphenylboronic anhydride; cyclopenten-1-yl boronic acid; 2-bromopyridine-3-boronic acid; 2,4-ditert-butoxypyrimidin-5-ylboronic acid; 2,4-bis(benzyloxy)pyrimidine-5-boronic acid; 5-phenyl-2-thienylboronic acid; 5-formylthiophene-3-boronic acid; or any combination thereof. In embodiments in which the chemical sensing moiety is a boronic acid or a boronic acid derivative, the sensed moiety may be a sugar. Example sugars may include glucose, galactose, maltose, lactose, fructose, sucrose, or any combination thereof. In one embodiment, where the chemical sensing moiety is boronic acid or a boronic acid derivative, the sensed moiety is glucose. In some embodiments, each biocompatible vesicle has only one kind of boronic acid or boronic acid derivative attached to it. In other embodiments, each biocompatible vesicle has either one kind of boronic acid or boronic acid derivative attached to it or more than one kind of boronic acid attached to it. Where different boronic acid derivatives are attached to each biocompatible vesicle, the crosslinkages formed by the different boronic acid derivatives may have different strengths. The degree of cleavage of crosslinks and the rate of release of the therapeutic compound may depend on the number of strong, weak, and moderate crosslinkages present.

In one embodiment, the triggering event may be hyperglycemia within the patient. In some embodiments, an increase in the glucose concentration in the physiological environment in the patient may trigger release of the therapeutic compound. In other embodiments, an increase in the sugar concentration in the physiological environment in the patient may trigger an increase in therapeutic compound released from the vesicle composition. In still other embodiments, the presence of sugar in the physiological environment may trigger the release of therapeutic compound in a quantity proportional to that of the sugar. In one embodiment, the sugar may be glucose, galactose, maltose, lactose, fructose, sucrose, or any combination thereof. In one embodiment, the sugar is glucose. In some embodiments, the triggering event may be when the sugar concentration in the physiological environment in the patient is greater than about 100 mg/dL.

In one embodiment, the vesicle composition may be administered between twice in one day to once a week, for an indefinite duration of days. In one embodiment, the vesicle composition may be administered once per day, for an indefinite duration of days. In some embodiments, the vesicle composition may be further characterized as being comprised of agglomerated vesicles.

In one embodiment, a method is provided for treating a medical condition, the method comprising administering a vesicle composition into a patient in need of treatment, the vesicle composition being loaded with a therapeutic compound for treatment of a patient in need thereof, and releasing the therapeutic compound into the patient in response to a triggering event. The vesicle composition may comprise biocompatible vesicles, one or more chemical sensing moieties, one or more sensed moieties, and crosslinks between the chemical sensing and sensed moieties. The vesicle composition may comprise an agglomeration of biocompatible vesicles. The vesicle composition may be administered by any suitable means, including, for example, by injection. Alternatively, the vesicle composition may be administered by pump or inhalation. In one embodiment, the vesicle composition may be administered between twice in one day to once a week, for an indefinite duration of days. In one embodiment, the vesicle composition may be administered once per day, for an indefinite duration of days.

Methods described herein may include administering a vesicle composition where the chemical sensor is a boronic acid or boronic acid derivative, the sensed moiety is a sugar, and the therapeutic compound is insulin. Boronic acid derivatives may include phenylboronates, pyridylboronates, and cyclohexylboronates. In one embodiment, the boronic acid derivative may comprise 3-(N,N-dimethylamino)phenyl boronic acid; 2,4-dichlorophenylboronic acid; 4-aminocarbonylphenylboronic acid; 3-chlorophenylboronic acid; 4-hydroxyphenylboronic acid; 4-propylphenylboronic acid; 3-[(E)-2-nitrovinyl)phenylboronic acid; 4-chlorocarbonylphenylboronic anhydride; cyclopenten-1-yl boronic acid; 2-bromopyridine-3-boronic acid; 2,4-ditert-butoxypyrimidin-5-ylboronic acid; 2,4-bis(benzyloxy)pyrimidine-5-boronic acid; 5-phenyl-2-thienylboronic acid; 5-formylthiophene-3-boronic acid; or any combination thereof. In embodiments in which the chemical sensing moiety is a boronic acid or a boronic acid derivative, the sensed moiety may comprise a sugar. Example sugars may include glucose, galactose, maltose, lactose, fructose, sucrose, or any combination thereof. In one embodiment where the chemical sensing moiety is boronic acid or a boronic acid derivative, the sensed moiety comprises glucose. In some embodiments, each biocompatible vesicle may have only one kind of boronic acid or boronic acid derivative attached to it. In other embodiments, each biocompatible vesicle may have either one kind of boronic acid or boronic acid derivative attached to it or more than one kind of boronic acid attached to it. Where different boronic acid derivatives are attached to each biocompatible vesicle, the crosslinkages formed by the different boronic acid derivatives may have different strengths. The degree of cleavage of crosslinks and the rate of release of the therapeutic compound may depend on the number of strong, weak, and moderate crosslinkages present.

Vesicle compositions may also include a targeting mechanism. The targeting mechanism may be any method of directing the vesicle composition to a specific destination within the patient's body. In one embodiment, the targeting mechanism may be a cell receptor, an antibody, a biomarker, or any combination thereof. In some embodiments, the vesicle composition may include a contrast agent, a diagnostic agent, or both.

A number of medical conditions may be treated by the inventive methods, including metabolic disorders. Examples of metabolic disorders may include any medical condition related to the body's metabolism, especially diabetes. A therapeutic compound for treating diabetes (e.g., insulin and its variants) is capable of sustaining normoglycemic levels for 24-72 hours. A normoglycemic level of sugar in the bloodstream is typically about 126 mg/dL.

The methods of the invention may also be used to treat pulmonary infection. When the methods of the invention are treating pulmonary infection, the therapeutic compound may be an antibiotic. The antibiotic may be any antibiotic suitable to treat pulmonary infection. In embodiments were the medical condition being treated is pulmonary infection, the therapeutic compound may be, for example, ciprofloxacin.

EXAMPLES

Example 1

NF-κB Assay for Inflammation

The inflammatory potential of various boronic acid compounds was studied by measuring the nuclear translocation of NF-κB in HeLa cells by immunocytochemistry and high throughput high contact microscopy. 15,000 HeLa cells were plated in 96 well plates the night before the experiments. On the day of the experiments, the cells were treated with the boronic acids (Table 1, below) at three different concentrations (40 nM, 80 nM, and 160 nM) for 2 h. At the end of the incubation, cells were washed with phosphate buffered saline (PBS) and were fixed in 4% paraformaldehyde for 15 min and permeablized with 0.01% Triton X-100 in PBS for 10 min. The cells were washed with PBS three times. Nonspecific sites were blocked with 5% bovine serum albumin (BSA) in PBS and incubated with the Anti-NF-κB for 1 h, followed by incubation with fluorescein isothiocyanate (FITC)-labeled secondary antibody. After washing the cells at the end of the incubation, the cells were treated with 4',6-diamidino-2-phenylindole (DAPI) for 1 min and kept at 4° C. until further analysis. Images of the cells were acquired with a Beckman-Coulter 100 automated high-throughput microscope system and analyzed using Cytseer software (Vala Sciences, CA.). The co-localization of NF-κB was quantified by measuring the PCC between the nuclear and cytoplasmic fraction of the NF-κB molecule. The PCC is a measure of the overlap between the pixel intensities of the nuclear and NF-κB images of the same cell. The PCC values can range from −1 to 1. A positive correlation (PCC value) indicates nuclear translocation of NF-κB. A negative correlation (negative PCC value) indicates an absence of nuclear translocation.

Figure 4:
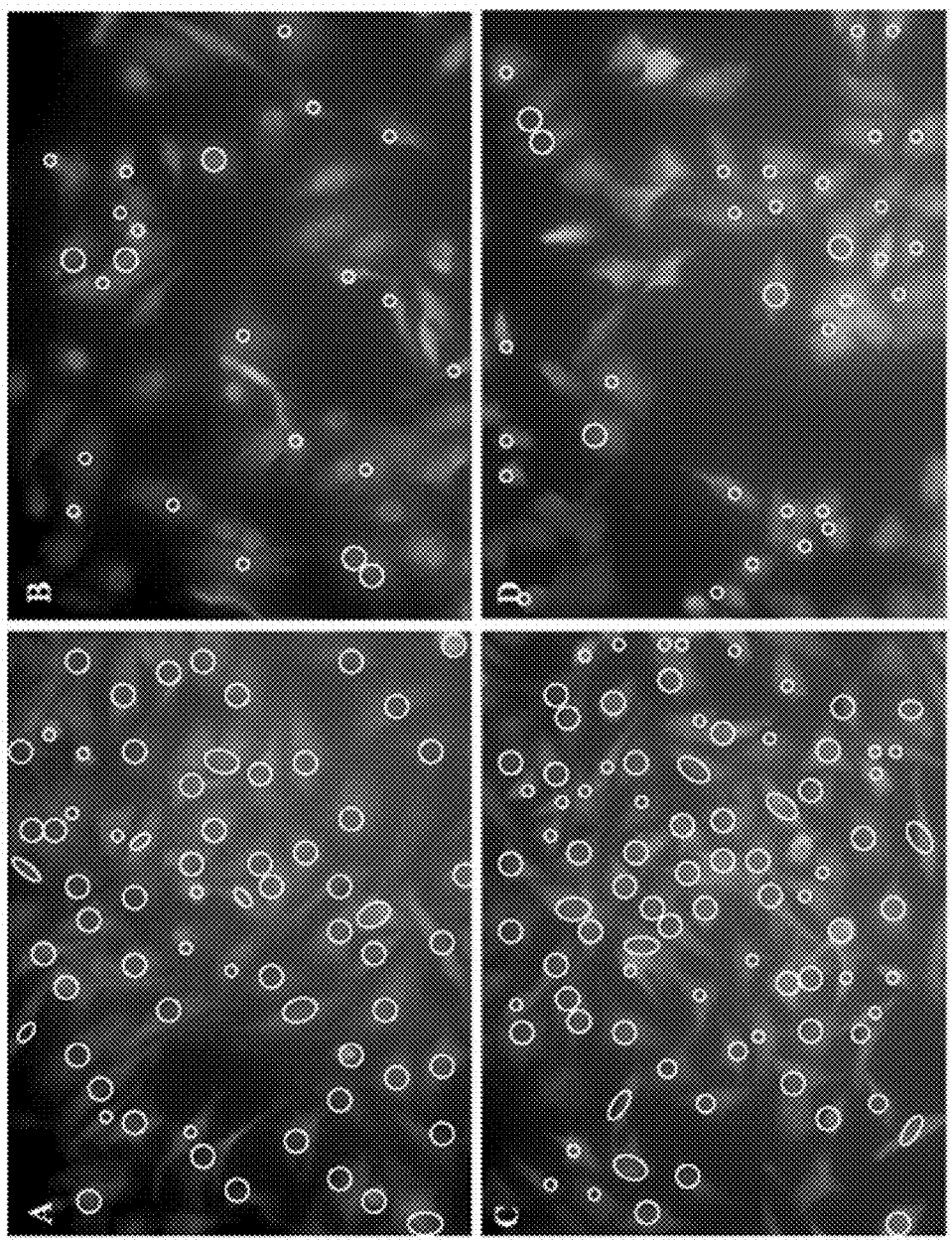
FIG. 4 shows representative images of HeLa cells showing the effect of boronic acid derivative treatment on the nuclear or cytoplasmic localization of NF-κB.
Figure 5A:
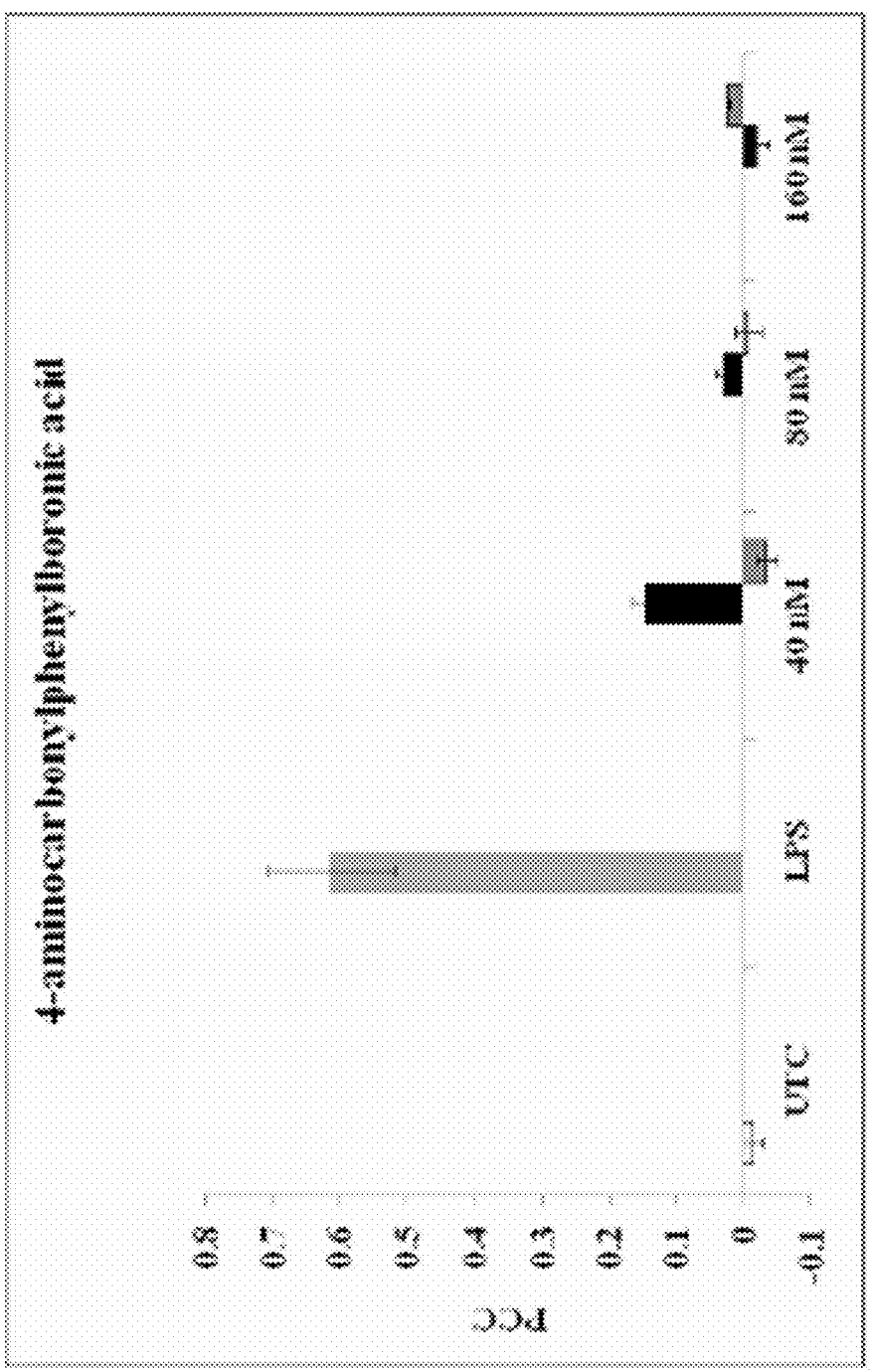
FIG. 5A demonstrates the Pearson's correlation coefficient (PCC) between the nuclear and cytoplasmic fractions of the NF-κB molecule in HeLa cells treated with free (dark bar) 4-aminocarbonylphenylboronic acid, as well as each of those boronic acid derivates as conjugates of DSPE-PEG-COOH (light bar), as compared to an untreated control (UTC) and lipopolysaccharide (LPS).
Figure 5B:
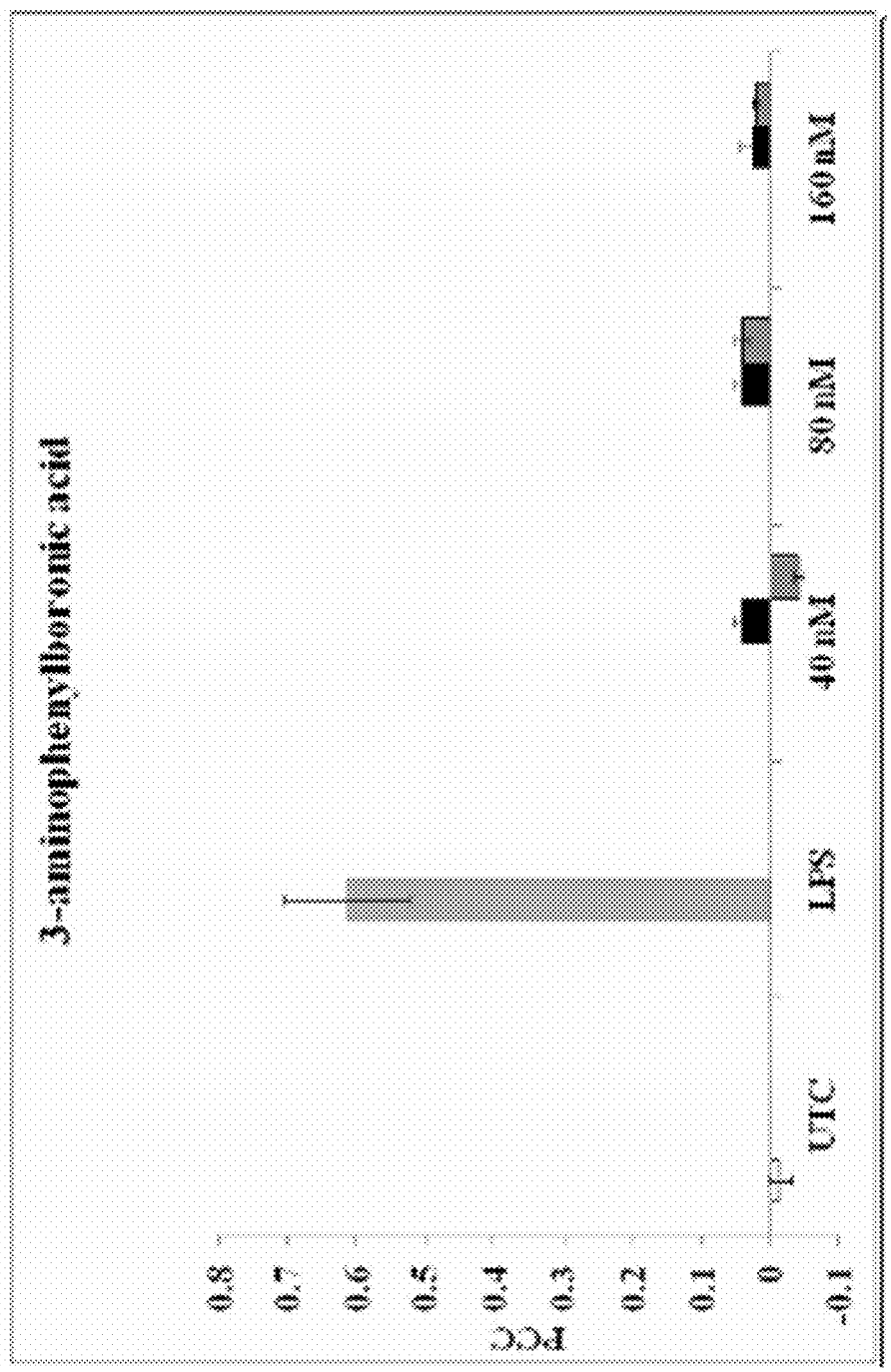
FIG. 5B demonstrates the Pearson's correlation coefficient (PCC) between the nuclear and cytoplasmic fractions of the NF-κB molecule in HeLa cells treated with free (dark bar) 3-aminophenylboronic acid, as well as each of those boronic acid derivates as conjugates of DSPE-PEG-COOH (light bar), as compared to an untreated control (UTC) and lipopolysaccharide (LPS).
Figure 5C:
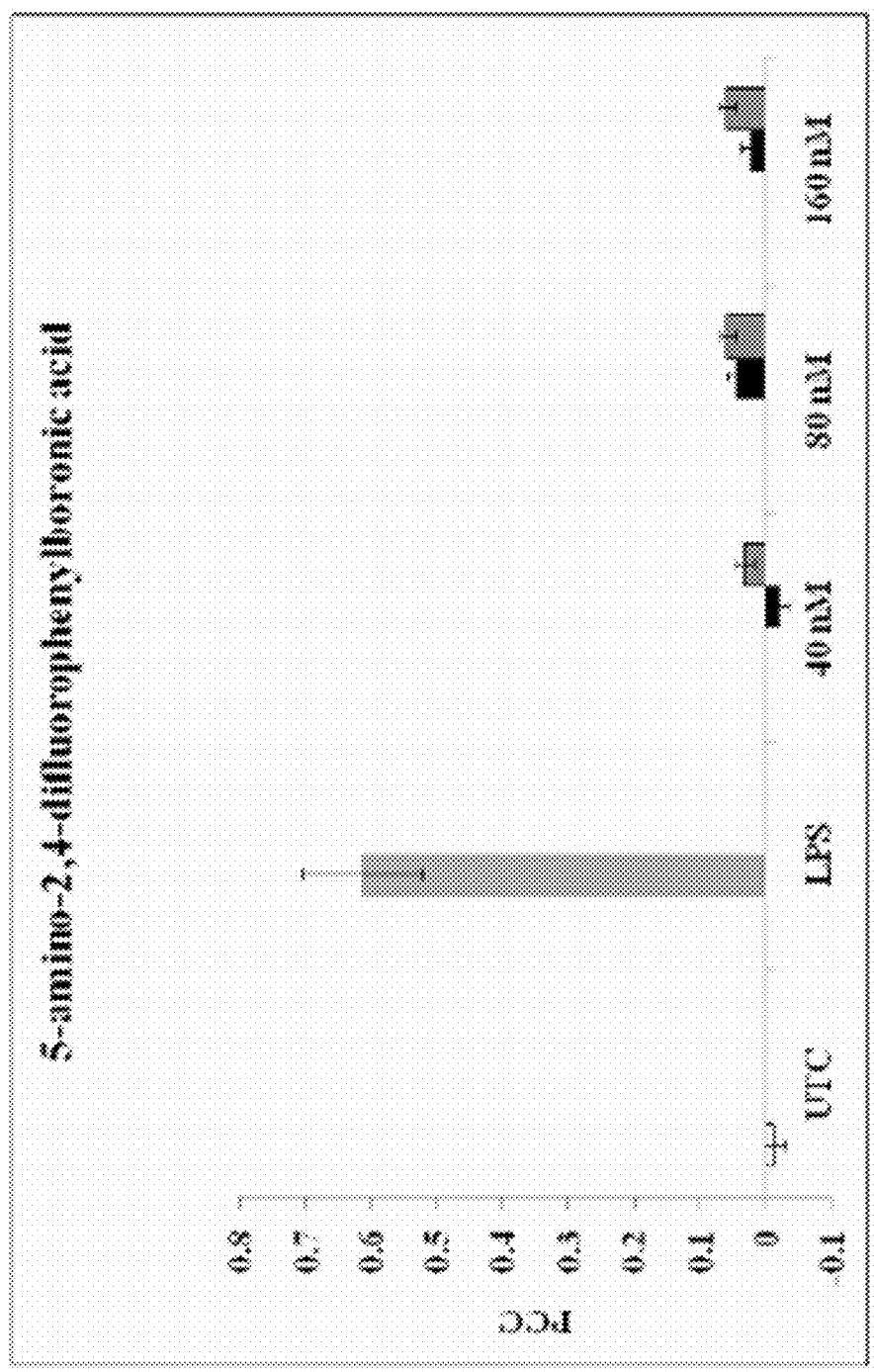
FIG. 5C demonstrates the Pearson's correlation coefficient (PCC) between the nuclear and cytoplasmic fractions of the NF-κB molecule in HeLa cells treated with free (dark bar) 5-amino-2,4-diflourophenylboronic acid, as well as each of those boronic acid derivates as conjugates of DSPE-PEG-COOH (light bar), as compared to an untreated control (UTC) and lipopolysaccharide (LPS).
Figure 5D:
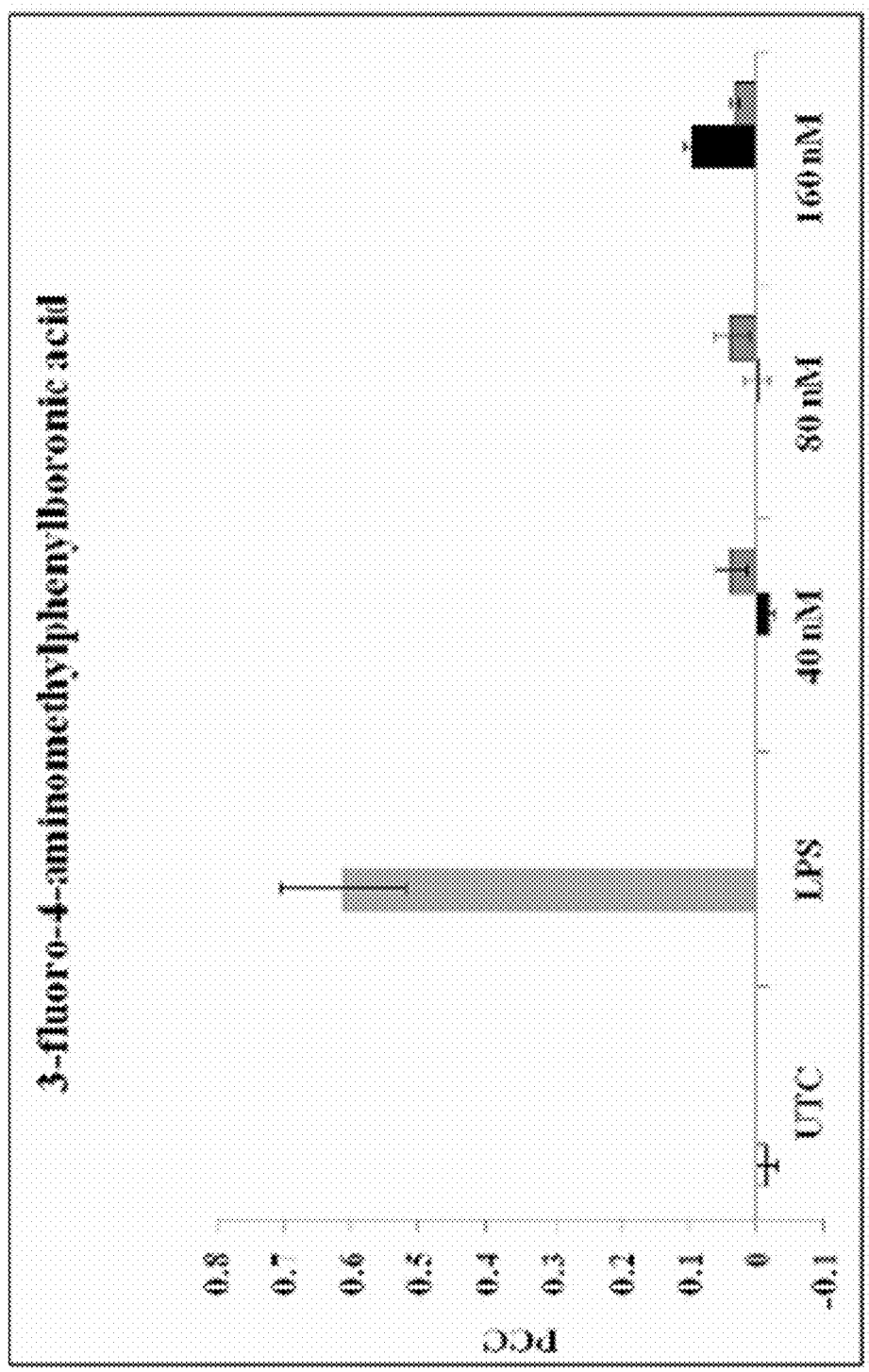
FIG. 5D demonstrates the Pearson's correlation coefficient (PCC) between the nuclear and cytoplasmic fractions of the NF-κB molecule in HeLa cells treated with free (dark bar) 3-fluoro-4-aminomethylphenylboronic acid, as well as each of those boronic acid derivates as conjugates of DSPE-PEG-COOH (light bar), as compared to an untreated control (UTC) and lipopolysaccharide (LPS).
Figure 5E:
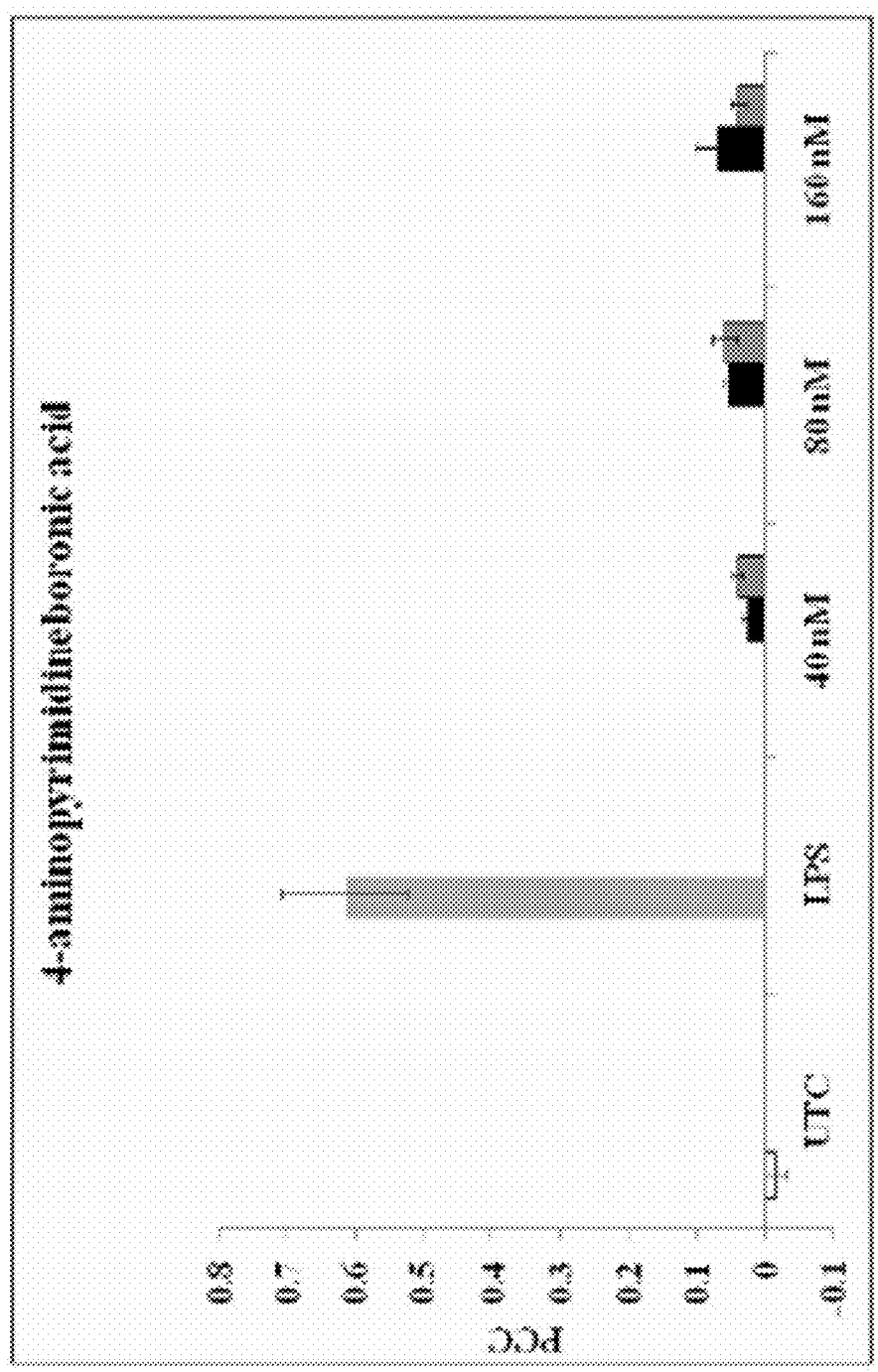
FIG. 5E demonstrates the Pearson's correlation coefficient (PCC) between the nuclear and cytoplasmic fractions of the NF-κB molecule in HeLa cells treated with free (dark bar) and 4-aminopyrimidineboronic acid, as well as each of those boronic acid derivates as conjugates of DSPE-PEG-COOH (light bar), as compared to an untreated control (UTC) and lipopolysaccharide (LPS).
Figure 6A:
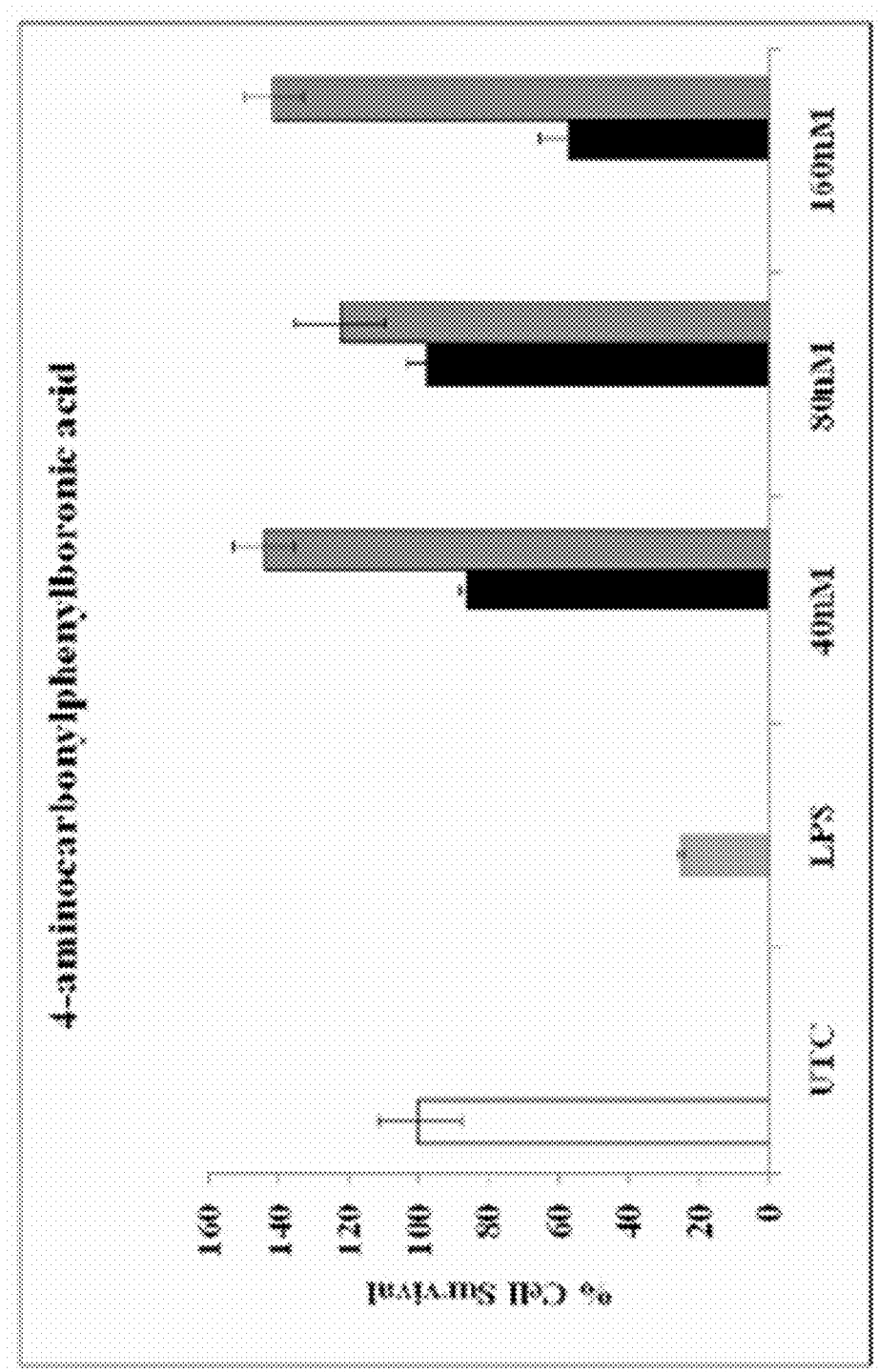
FIG. 6A demonstrates the surviving fractions of HeLa cells treated with free (dark bar) 4-aminocarbonylphenylboronic acid, as well as each of those boronic acid derivates as conjugates of DSPE-PEG-COOH (light bar), as compared to a UTC and LPS.
Figure 6B:
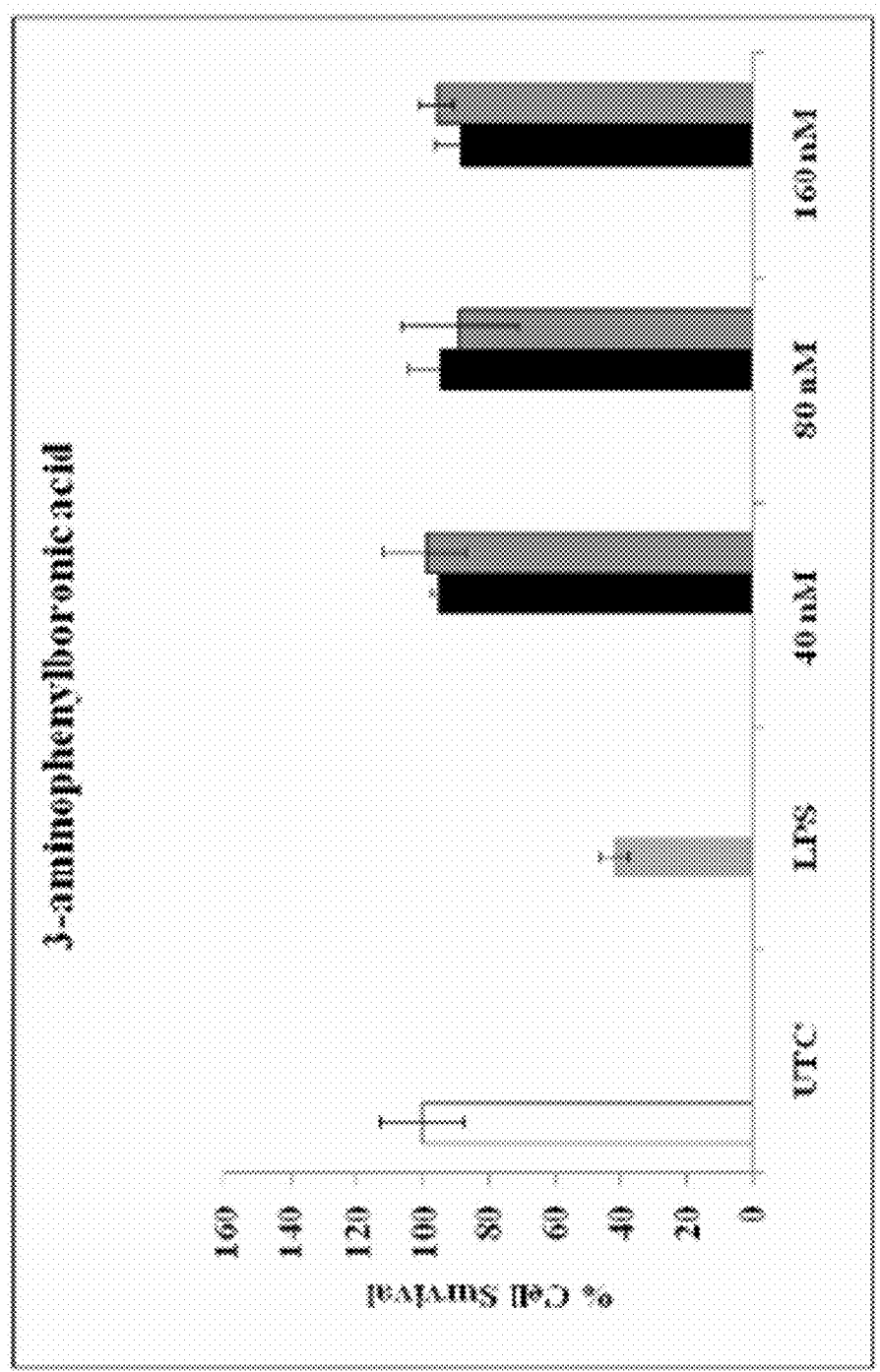
FIG. 6B demonstrates the surviving fractions of HeLa cells treated with free (dark bar) 3-aminophenylboronic acid, as well as each of those boronic acid derivates as conjugates of DSPE-PEG-COOH (light bar), as compared to a UTC and LPS.
Figure 6C:
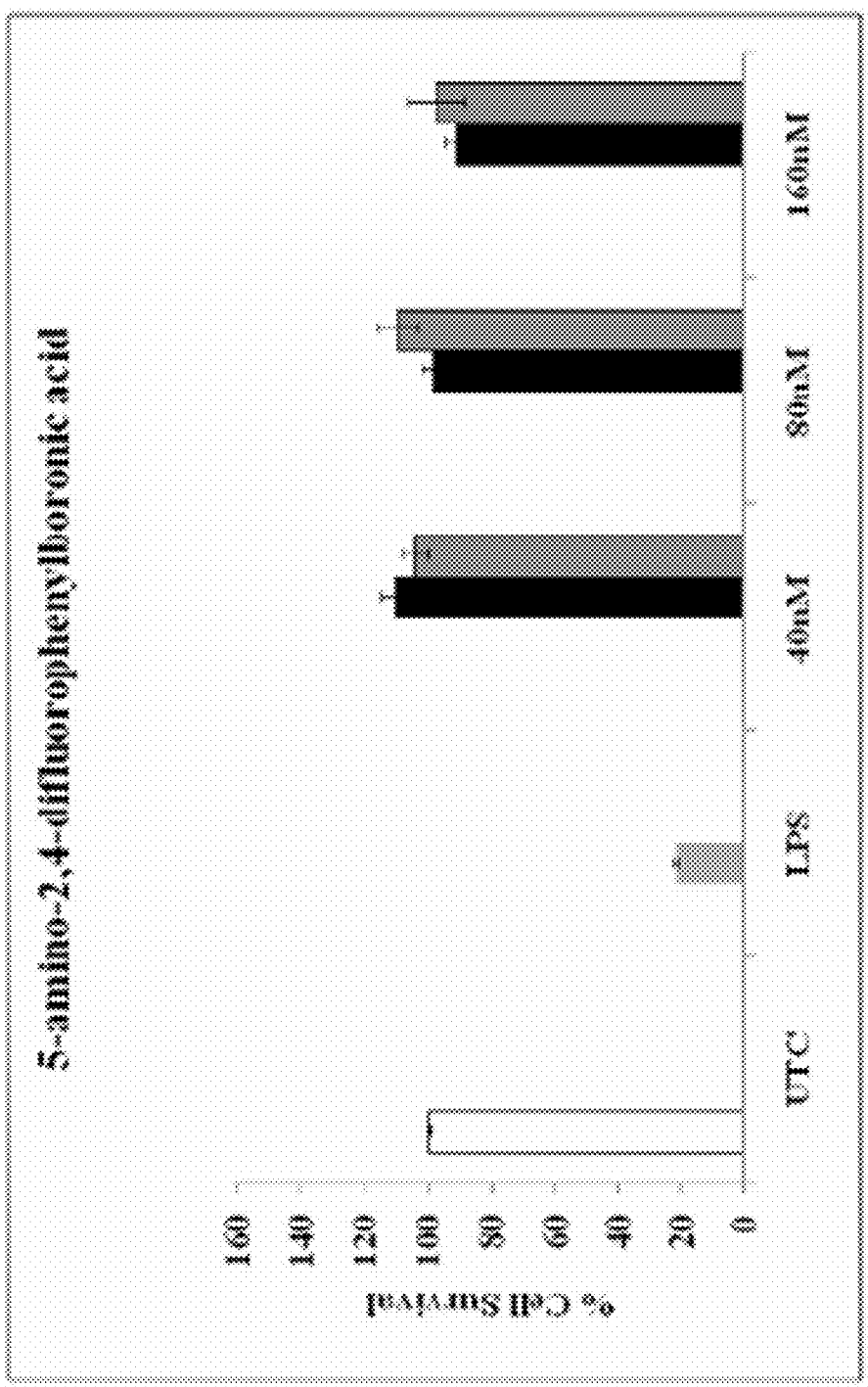
FIG. 6C demonstrates the surviving fractions of HeLa cells treated with free (dark bar) 5-amino-2,4-diflourophenylboronic acid, as well as each of those boronic acid derivates as conjugates of DSPE-PEG-COOH (light bar), as compared to a UTC and LPS.
Figure 6D:
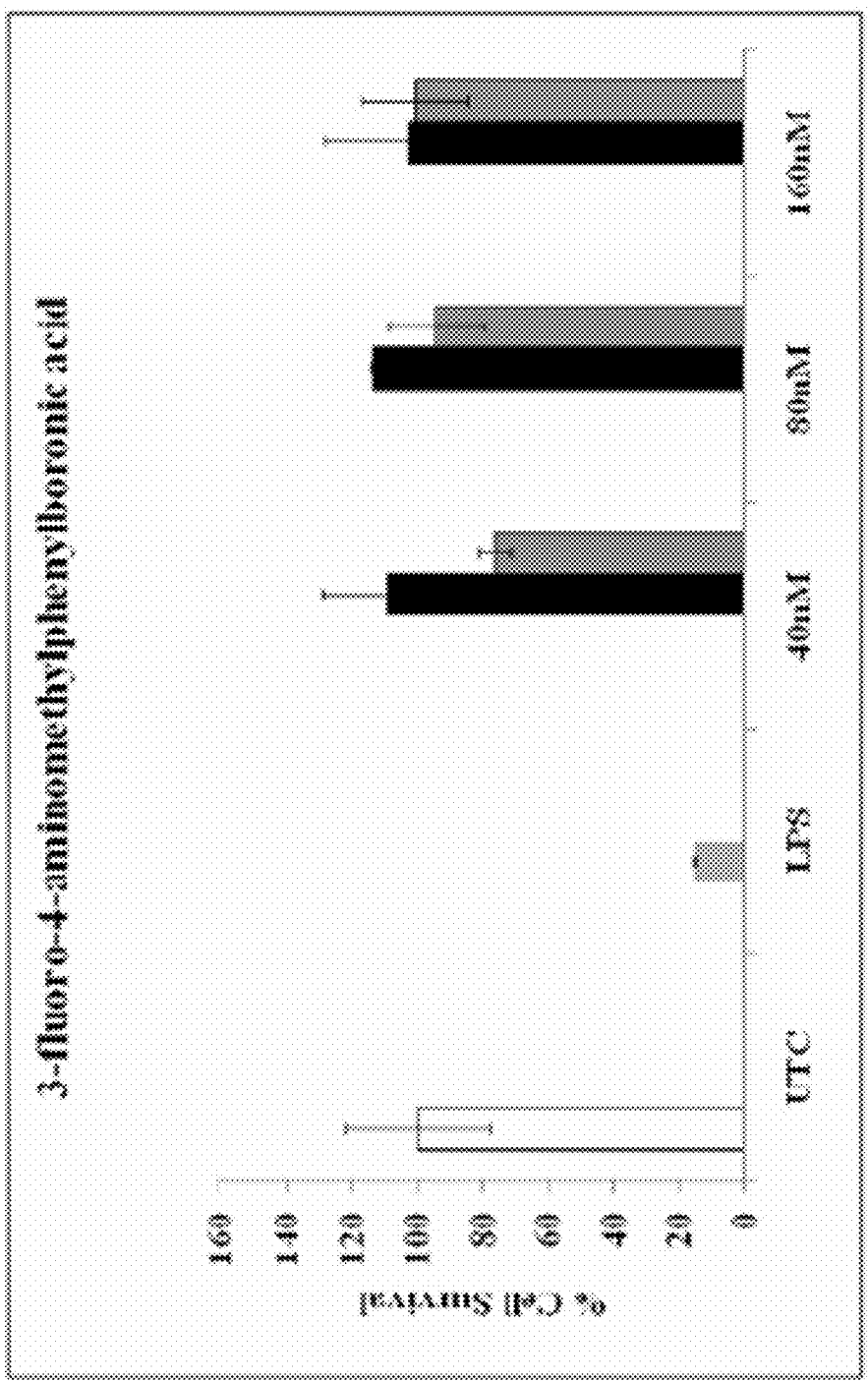
FIG. 6D demonstrates the surviving fractions of HeLa cells treated with free (dark bar) 3-fluoro-4-aminomethylphenylboronic acid, as well as each of those boronic acid derivates as conjugates of DSPE-PEG-COOH (light bar), as compared to a UTC and LPS.
Figure 6E:
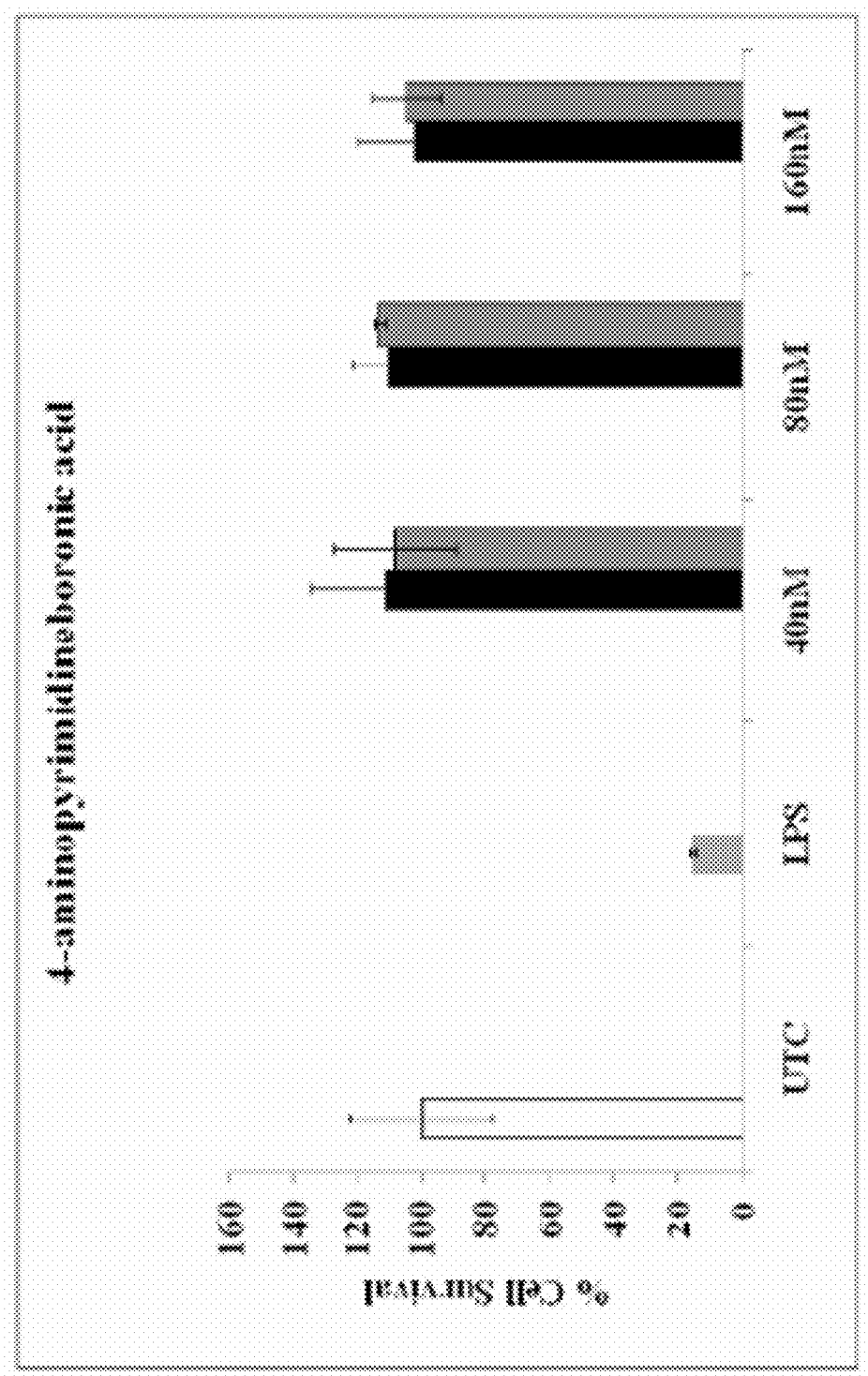
FIG. 6E demonstrates the surviving fractions of HeLa cells treated with free (dark bar) 4-aminopyrimidineboronic acid, as well as each of those boronic acid derivates as conjugates of DSPE-PEG-COOH (light bar), as compared to a UTC and LPS.

FIG. 4 shows representative images of HeLa cells illustrating the effect of boronic acid treatment on the nuclear or cytoplasmic localization of NF-κB. DAPI is shown by white circles, while NF-κB is represented by light gray. White circles surrounded by light gray indicate cytoplasmic NF-κB, while obliteration of the white circles by the gray signal in the nucleus indicates nuclear NF-κB. (A) UTC, cytoplasmic NF-κB; (B) Positive control, nuclear translocation of NF-κB in cells treated with LPS; (C) Treatment with 2,4-di(tert-butoxy) pyrimidine-5-yl-boronic acid (80 nM, 2 hrs), predominantly cytoplasmic NF-κB; and (D) Treatment with 5-isoquinolineboronic acid (80 nM, 2 hrs.), predominantly nuclear NF-κB.

FIG. 5 demonstrates the PCC between the nuclear and cytoplasmic fractions of the NF-κB molecule in HeLa cells treated with free (dark bar) 4-aminocarbonylphenylboronic acid, 3-aminophenylboronic acid, 5-amino-2,4-diflourophenylboronic acid, 3-fluoro-4-aminomethylphenylboronic acid, and 4-aminopyrimidineboronic acid, as well as each of those boronic acid derivates as conjugates of DSPE-PEG-COOH (light bar), as compared to a UTC and LPS. Surprisingly, the 4-aminocarbonylphenylboronic acid conjugate was less inflammatory than free 4-aminocarbonylphenylboronic acid.

Table 1 and FIG. 8 list the PCC results for various boronic acid derivatives.

TABLE 1

| | MTT (% Cell Survival) | | | Inflammation (PCC) | | | Sugar Binding Affinity $\text{Log}(\text{Ka}_{BA}/\text{Ka}_{ConA})$ |
|---|---|---|---|---|---|---|---|
| | 40 nM | 80 nM | 160 nM | 40 nM | 80 nM | 160 nM | |
| 2-bromopyridine-5-boronic acid | 95.1013 | 120.589 | 35.78268877 | 0.00604 | 0.078 | 0.144556 | |
| 3-(N,N-dimethylamino)phenyl boronic acid | 123.37 | 86.2247 | 85.91160221 | −0.1236 | −0.0401 | 0.186204 | −0.14 |
| 2-napthylboronic acid | 24.3831 | 37.2192 | 21.10497238 | 0.06402 | 0.24369 | 0.095931 | |
| 3-carboxy-5-nitrophenylboronic acid | 54.3094 | 46.2431 | 33.29650092 | −0.0136 | 0.03893 | 0.122719 | |
| uracil-5-boronic acid | 68.5083 | 50.3499 | 28.06629834 | −0.0586 | 0.00516 | −0.015223 | |
| 2-chloro-3-quinolineboronic acid | 30.1105 | 44.7882 | 32.43093923 | 0.08644 | 0.05095 | 0.192957 | |
| 2-propoxyphenylboronic acid | 45.7459 | 42.2099 | 41.95211786 | −0.0398 | 0.03035 | −0.049539 | |
| 2-cyanophenylboronic acid | 117.42 | 62.63 | 60.33 | −0.0641 | 0.0475 | 0.104 | |
| 2,4-dicholorophenylboronic acid | 99.29 | 81.59 | 79.9 | −0.0502 | 0.09386 | 0.3067 | −0.93 |
| thianthrene-1-boronic acid | 64.19 | 61.32 | 81.10 | −0.0683 | 0.0268 | 0.109448 | |
| cyclopropylboronic acid | 81.55 | 107.79 | 80.01 | −0.0484 | 0.03475 | 0.170472 | |
| 2,6-dimethoxyphenylboronic acid | 92.66 | 78.05 | 48.60 | −0.0679 | 0.03888 | 0.260667 | |
| 3-aminocarbonylphenylboronic acid | 101.02 | 77.93 | 29.19 | −0.0696 | 0.07022 | 0.174824 | |
| 3-(benzyloxy)phenylboronic acid | 99.83 | 71.94 | 28.92 | −0.1159 | 0.0809 | 0.376808 | |
| 3-nitrophenylboronic acid | 58.14 | 55.55 | 38.03 | −0.0801 | 0.06937 | 0.233508 | |
| 4-cyanophenylboronic acid | 60.40 | 63.69 | 54.22 | −0.0705 | −0.204 | 0.487922 | |
| 4-aminocarbonylphenylboronic acid | 86.57 | 97.67 | 57.28 | −0.0838 | 0.01211 | 0 | −1.03 |
| 3-cyano-4-fluorophenylboronic acid | 89.30 | 60.46 | 47.56 | −0.0231 | 0.10144 | 0 | |
| 2-chloropyridine-4-boronic acid | 84.93 | 58.47 | 56.36 | −0.1195 | 0.00374 | 0 | |
| 3-hydroxyphenylboronic acid | 104.60 | 62.75 | 89.29 | −0.1136 | 0.04005 | 0 | |
| trans-2-Phenylvinylboronic acid | 72.90 | 99.51 | 65.87 | −0.1303 | 0.15234 | 0 | |
| 4-chlorophenylboronic acid | 51.23 | 81.65 | 56.97 | −0.1494 | 0.01664 | 0 | |
| 1-phenylvinylbornic acid | 66.08 | 67.23 | 58.91 | −0.1145 | 0.03776 | 0 | |
| 2-thienylboronic acid | 53.48 | 75.76 | 61.19 | −0.121 | −0.0343 | 0 | |
| 4-(dimethylamino)phenylboronic acid | 78.59 | 71.75 | 51.04 | −0.1318 | −0.0051 | 0.212957 | |

TABLE 1-continued

| | MTT (% Cell Survival) | | | Inflammation (PCC) | | | Sugar Binding Affinity Log($Ka_{BA}$/$Ka_{ConA}$) |
|---|---|---|---|---|---|---|---|
| | 40 nM | 80 nM | 160 nM | 40 nM | 80 nM | 160 nM | |
| 1-(triisopropylsilyl)pyrrol-E-3-boronic acid | 72.92 | 65.92 | 56.94 | −0.0781 | 0.00445 | 0.16903. | |
| 5-bromopyridine-3-boronic acid | 134.748 | 37.2764 | 30.03715319 | −0.038 | 0.13112 | 0.291325 | |
| 3-chlorophenylboronic acid | 97.1779 | 73.129 | 38.55244882 | −0.0824 | 0.03311 | 0.396508 | −1.03 |
| N-methylindole-2-boronic acid | 63.3131 | 63.6075 | 47.46038056 | −0.126 | 0.00746 | 0.133554 | |
| N-boc-2-pyrroleboronic acid | 60.6873 | 51.264 | 39.41134031 | −0.0675 | 0.05743 | 0.183701 | |
| 2-hydroxyphenylboronic acid | 70.3314 | 55.8039 | 53.64439929 | −0.0198 | −0.0878 | 0.088843 | |
| 2-formyl-3-thopheneboronic acid | 55.3376 | 40.3684 | 46.20885296 | −0.0993 | −0.0793 | 0.126198 | |
| 2-chlorophenylboronic acid | 86.3068 | 60.0002 | 45.4481205 | −0.0957 | .00949 | 0.099477 | |
| 4-hydroxyphenylboronic acid | 203.926 | 198.184 | 172.8339984 | −0.0665 | −0.1081 | 0.200707 | −1.08 |
| 4-propylphenylboronic acid | 202.674 | 202.92 | 164.1960039 | −0.1402 | −0.0786 | 0.192226 | −0.009 |
| 5-isoquinolineboronic acid | 75.80 | 60.84 | 41.69 | −0.0412 | 0.02463 | 0.278406 | |
| 5-fluoro-2-methoxyphenylboronic acid | 84.22 | 84.22 | 54.92 | −0.0169 | 0.02474 | 0.293611 | |
| pentafluorophenylboronic acid | 65.63 | 60.00 | 50.98 | 0.0154 | 0.0762 | 0.258448 | |
| 5-formyl-2-furanboronic acid | 77.18 | 94.08 | 50.14 | 0.00989 | −0.0122 | 0.113246 | |
| 5-acetyl-2-thiopheneboronic acid | 84.50 | 82.81 | 51.27 | 0.02454 | 0.06312 | 0.23431 | |
| 3-thienylboronic acid | 90.42 | 80.00 | 49.85 | −0.0062 | 0.14569 | 0.059629 | |
| 5-cyanothiophene-2-boronic acid | 80.56 | 40.00 | 44.78 | −0.01 | 0.10511 | 0.24335 | |
| 4-ethylsulfonyl-phenylboronic acid | 67.61 | 66.47 | 37.46 | 0.00184 | 0.1802 | 0.129047 | |
| 5-bromobenzo-B-thophene-2boronic acid | 71.83 | 81.40 | 90.42 | −0.0244 | −0.01 | 0.126527 | |
| 2-ethoxy-5-pyridine-boronic acid | 81.40 | 69.58 | 33.80 | −0.1416 | −0.0136 | 0.149833 | |
| 2-(N,N-dimethylsulphamoyl)benzeneboronic acid | 74.92 | 76.38 | 47.32 | −0.1529 | −0.0404 | 0.034217 | |
| 3-bromothiophene-4-boronic acid | 76.45 | 95.90 | 97.49 | −0.0695 | 0.15676 | 0.152756 | |
| 3-bromothiophene-5-boronic acid | 116.67 | 97.63 | 62.08 | −0.1162 | −0.023 | 0.153863 | |
| 3-[(E)-2-nitrovinyl]phenylboronic acid | 116.00 | 96.38 | 73.93 | −0.0456 | −0.0517 | 0.205842 | NA |
| 5-formylthiophene-3-boronic acid | 86.87 | 87.03 | 73.80 | −0.0359 | 0.00225 | 0.193025 | −1.24 |
| 4-chlorocarbonylphenylboronic anhydride | 114.54 | 107.21 | 79.46 | −0.0664 | −0.0012 | 0.098262 | −2.08 |
| cyclopenten-1-yl boronic acid | 99.21 | 79.90 | 68.16 | −0.0551 | 0.01168 | 0.163417 | NA |
| 2-bromopyridine-3-boronic acid | 102.96 | 94.00 | 87.88 | −0.0553 | −0.0396 | 0.149396 | −2.9 |
| 2,4-di-tert-butoxypyrimidin-5-ylboronic acid | 100.46 | 90.60 | 71.81 | −0.0888 | 0.03106 | 0.172566 | 0.008 |
| 2,4-bis(benzyloxy)pyrimidine-5-boronic acid | 100.05 | 89.04 | 74.74 | −0.0647 | −0.0533 | 0.04709 | NA |
| 3-formylfuran-2-boronic acid | 107.84 | 73.72 | 65.18 | −0.0012 | 0.0274 | 0.086213 | |
| 5-phenyl-2-thienylboronic acid | 100.56 | 81.24 | 86.23 | −0.0211 | −0.0701 | 0.118672 | −2.3 |
| 1-benzyl-1H-pyrazole-4-boronic acid | 100.88 | 62.54 | 86.11 | −0.1081 | −0.0841 | 0.03839 | |
| 4-dibenzofuranboronic acid | 71.48 | 75.50 | 70.50 | −0.0736 | −0.0438 | −0.127966 | |
| 3,5-dimethylisoxazole-4-boronic acid | 88.37 | 90.63 | 42.89 | −0.061 | 0.0057 | −0.012768 | |
| 5-cyano-2-methoxyphenylboronic acid | 81.55 | 49.84 | 62.08 | −0.0808 | −0.0523 | −0.080857 | |
| diisopropyl(bromomethyl)boronate | 81.27 | 96.62 | 79.32 | −0.0205 | 0.02739 | 0.11569 | |

Example 2

MTT Assay for Cytotoxicity

The cytotoxicity of the boronic acid derivatives from Table 1 was studied by MTT assay. 150,000 HeLa cells were plated in 96 well plates on the night before the experiments. On the day of experiments, the cells were treated with the boronic acid derivatives at three different concentrations (40 nM, 80 nM, and 160 nM) for 2 h. At the end of the incubation, MTT assays (In-Vitro toxicology MTT based assay kit, Sigma Aldrich, MO) were performed according to the manufacturer's protocol.

FIG. 6 demonstrates the surviving fractions of HeLa cells treated with free (dark bar) 4-aminocarbonylphenylboronic acid, 3-aminophenylboronic acid, 5-amino-2,4-diflourophenylboronic acid, 3-fluoro-4-aminomethylphenylboronic acid, and 4-aminopyrimidineboronic acid, as well as each of those boronic acid derivates as conjugates of DSPE-PEG-COOH (light bar), as compared to a UTC and LPS. Surprisingly, the 4-aminocarbonylphenylboronic acid conjugate was less cytotoxic than free 4-aminocarbonylphenylboronic acid.

Table 1 and FIG. 8 list the cell survival rate for various boronic acid derivatives.

Example 3

Binding Assay

The binding affinity of boronic acid derivatives to glucose was determined by competition assay using ConcanavalinA (ConA) as the competitive standard, and varying concentrations of the boronic acid derivatives. Carboxy-terminated magnetic beads were activated by suspending the beads in 100 mM 2-(N-morpholino)ethanesulfonic acid (MES) buffer (pH 4.5). Glucosamine (100 mg/mL) was conjugated to the activated magnetic beads using carbodiimide coupling with 1-ethyl-3-(3-dimethylaminopropyl) carbodiimide (EDC) as a crosslinker. The conjugation reaction was carried out in a 96 well plate. The reaction was run for 24 h. The beads were separated by placing the microplate on a magnetic separator and were washed thoroughly with PBS at pH 7.2 to remove unbound glucose, excess EDC, and N-hydroxysulfosuccinimide (Sulfo-NHS).

The glucose terminated beads were co-incubated for 1 h with 2.4 µM ConA (a known binder of carbohydrates) fluorescently tagged with fluorescein isothiocyanate (ConA-FITC), and titrated with concentrations ranging from 2.5 µM to 20 µM of each boronic acid derivative tested. The following controls were used: (A) carboxy-terminated magnetic beads (not conjugated to glucose) were treated with ConA-FITC to determine non-specific binding; and (B) glucose conjugated beads were treated with a high concentration of non-fluorescent ConA to determine maximal binding.

The wells were washed three times with PBS at pH 7.2 to remove unbound boronic acid derivatives and FITC-ConA. The beads were re-suspended in PBS and stirred for 15 min at rt before measuring FITC fluorescence (excitation: 495 nm, top emission: 520 nm; 6 flashes per well; average of n=3 wells in a Flexstation II$^{384}$ microplate reader to quantify the amount of glucose bound to the boronic acids. The fluorescence intensity was measured and used as an indication of the amount of ConA bound to the surface of the beads, or [ConAs]. The ConA-sugar interaction was expected to be inhibited by the boronic acid derivatives, which can bind the sugar molecules and displace the bound ConA-FITC, thereby causing a decrease in fluorescence intensity of the mixture.

The binding constant of the boronic acid derivatives was calculated from the fluorescence intensity. The reduction of fluorescence intensity is related to [ConAs] by Equation 2.

$$[ConA_s] = \left(1 - \frac{F_{max} - F_{obs}}{F_{max}}\right) * [ConA_s] \quad (Eq.\ 2)$$

The relationship between [ConAs] and the amount of boronic acid [BA] is given by Equation 3.

$$[ConA_s] = \frac{S_t \cdot [ConA]}{1 + \frac{[BA] \cdot K\alpha_{ConA}}{[ConA] \cdot K\alpha_{BA}}} \quad (Eq.\ 3)$$

Simple rearrangement yields Equation 4, from which the ratio of the two equilibrium constants ($K_{ConA}/K_{BA}$) can be derived.

$$\frac{1}{[ConA_s]} = \frac{1}{S_t} + \frac{[BA]}{[ConA]S_t} * \frac{Ka_{ConA}}{Ka_{BA}} \quad (Eq.\ 4)$$

The concentration of sugar sites (S1) can be calculated from the intercept of a plot of 1/[ConAs] vs 1/[BA].

Figure 7:
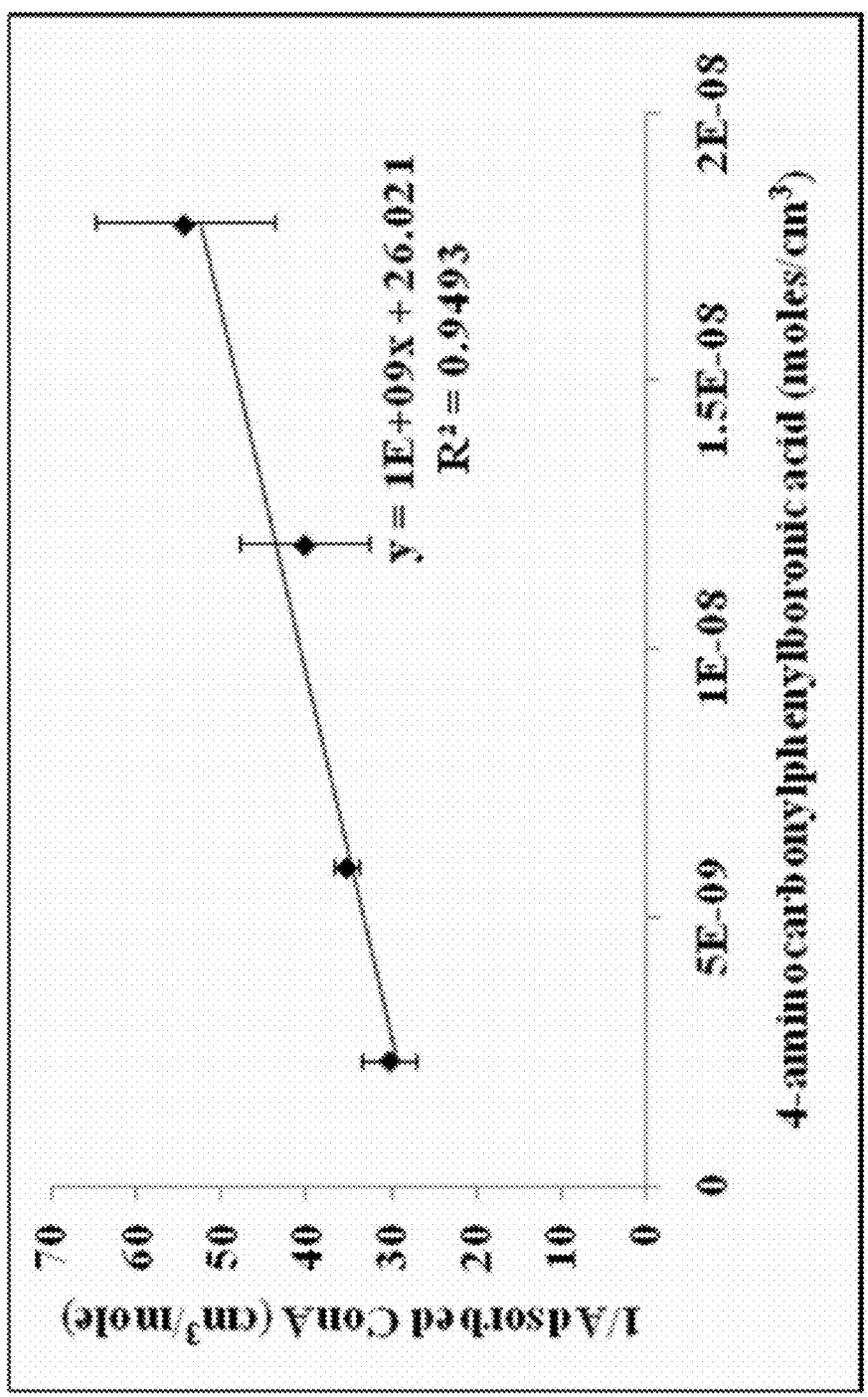
FIG. 7 shows a representative plot for the binding constant calculation for 4-aminocarbonylphenylboronic acid.

FIG. 7 shows a representative plot for the binding constant calculation for 4-aminocarbonylphenylboronic acid.

Table 1 lists the relative sugar binding affinities (log ($K_{ConA}/K_{BA}$)) of various boronic acid derivatives, compared to ConA.

FIG. 8 shows the structure and glucose binding affinity ($M^{-1}$) for various boronic acid derivatives.

Example 4

Synthesis of Lipid-PEG-Linker-Boronic Acid Conjugates

All lipid-PEG-linker-boronic acid and sugar conjugates were prepared by coupling the amine-derivative of the boronic acid-linker or sugar moieties, with DSPE-PEG-COOH using carbodiimide chemistry. In general, 50 mg of DSPE-PEG-COOH were dissolved in 2 mL anhydrous dimethylformamide (DMF), followed by the addition of EDC (2.0 equivalents) and N-Hydroxysuccinimide (NHS) (3.0 equivalents), and the mixture was allowed to stir for 30 min at rt. The amine derivative of the boronic acid or sugar was added and the reaction mixture was allowed to stir overnight. For amines obtained in the form of the ammonium salt, these were de-salted by stirring in 500 µL DMF and 35 µL triethylamine for 30 min at rt prior to addition to the reaction mixture. The reaction mixture was diluted with 4 mL MES buffer (50 mM, pH 4.18), transferred into a 3K MWCO dialysis cassette, and dialyzed twice against 2 L of the same buffer, then twice against 2 L water, followed by freeze drying to obtain the desired conjugate. The identity and purity of the final product was confirmed by $^1$H NMR spectrometry.

Example 5

Synthesis of Liposomes Functionalized with Sugar/Boronic Acids and Their Conjugates Synthesis of Phospholipid-Polyethylene Glycol-Gyclosyl Conjugates.

Lipid-PEG-Glycosyl species were synthesized by conjugating the carboxyl group of DSPE-PEG-COOH to the amino group of glucosamine, galactosamine, and mannopyranoside, using the carbodiimide coupling chemistry described in G. T. Hermanson, Bioconjugate Techniques, Academic Press, Elsevier Science USA (1996) 169-185, incorporated herein by reference. The coupling was done at the C2 position of the sugar molecules, thereby keeping the C3, C4, and C5 positions unmodified.

Loading of Liposomes with Insulin.

Human recombinant insulin was dissolved in citrate buffer (100 mM, pH 2.5) to a concentration of 15 mg/mL. Lipids (56.4 mole % DPPC, 40 mole % cholesterol, and 1.2 mole % each of DSPE-PEG-Glucose, DSPE-PEG-Galactose, DSPE-PEG-Mannopyranoside) were dissolved in ethanol and hydrated with the insulin solution at 50° C. for 15 min. The final lipid concentration was 50 mM. The hydrated mixture was passed eight times through a 400 nm Nucleopore track-etch membrane at 50° C. at a pressure of 100 psi. The parent liposomes had a mean diameter of 244.1 nm (suitable average liposome diameters may be from about 100 nm to about 300 nm) and a lipid concentration of about 50 mM. Insulin was encapsulated by passive loading. The pH of the liposomal formulation was maintained at 5.6 (isoelectric point of insulin). The liposomes were dialyzed against citrate buffer (100 nM, pH 5.6) to remove the unencapsulated insulin. In this example, unencapsulated insulin is removed to mitigate or prevent the insulin from having an immediate and, perhaps, unnecessary effect upon the physiological environment. In some embodiments, the vesicle composition is intended to release and/or provide insulin primarily or solely in response to the presence of a threshold amount of glucose in the physiological environment of the patient (i.e., having a "glucose responsive" effect), such as when the patient is experiencing a hyperglycemic condition. In the instant example, the encapsulated insulin was present in a concentration of approximately 15 mg/mL, although it is contemplated that the concentration of the encapsulated insulin may be approximately the same as, or may be less than or greater than, the starting concentration of insulin. The unencapsulated insulin may be present in a concentration of approximately 0%-5% of the encapsulated insulin, or up to about 0.75 mg/mL, although higher concentrations of unencapsulated insulin may be acceptable or preferred, depending on the patient's need and the medium by which the vesicle composition is introduced into the physiological environment of the patient.

Synthesis of Phospholipid-Polyethylene Glycol-Boronic Acid Derivative Conjugates.

Lipid-PEG-boronic acid was synthesized by conjugating the carboxyl group of DSPE-PEG-COOH to the amino functionalized boronic acid moieties using the carbodiimide coupling chemistry described in G. T. Hermanson, Bioconjugate Techniques, Academic Press, Elsevier Science USA (1996) 169-185, incorporated herein by reference. The lipid composition for the boronic acid functionalized liposome was the following: 56.4 mole % DPPC, 40 mole % cholesterol, and 3.6 mole % of DSPE-PEG-boronic acid.

Representative lipid-PEG-boronic acid derivative conjugate species include:

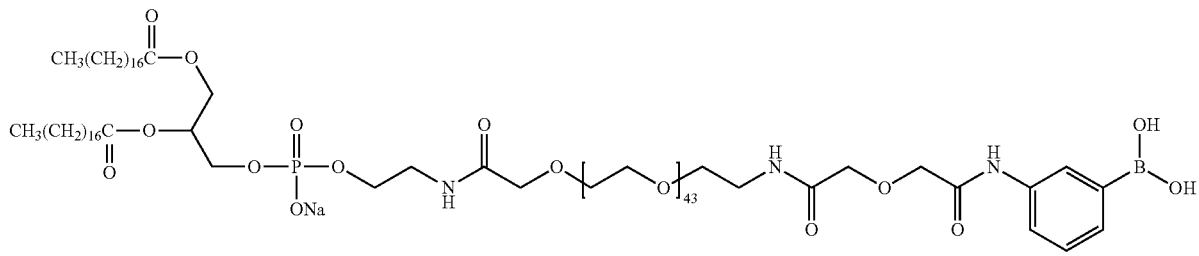

3-Aminophenylboronic acid conjugate

Characteristic $^1$H NMR peaks: δ ppm 7.98 (s, 1H), 7.59 (d, 1H), 7.31 (d, 1H), 7.03 (t, 1H), 5.33 (s, 1H, NH), 5.21 (s, 2H, NH), 1.55 (t, 3H), 1.49 (t, 3H).

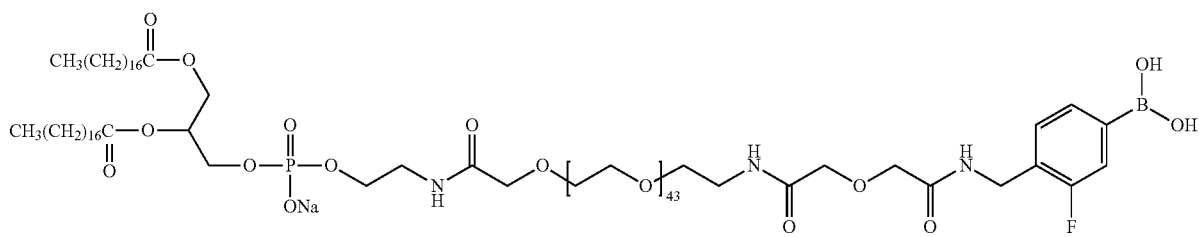

3-Fluoro-4-aminomethylphenylboronic acid conjugate

Characteristic $^1$H NMR (300 MHz, acetone-d6) peaks: δ ppm 8.15 (d, 1H), 8.00 (dd, 1H), 7.90 (m, 1H), 5.70 (s, 1H, NH), 5.50 (s, 1H, NH), 1.55 (t, 3H), 1.40 (t, 3H).

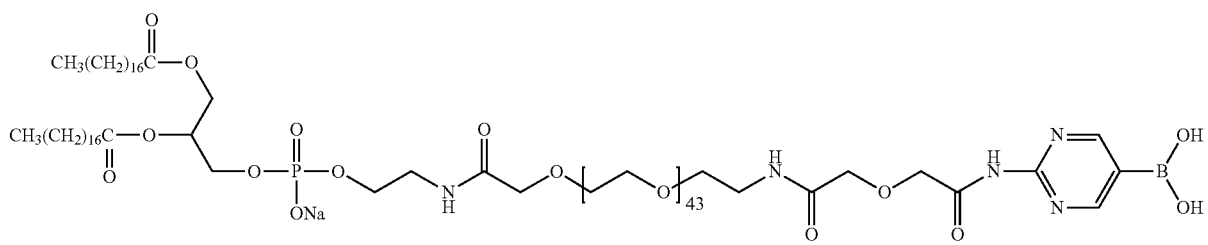

4-Aminopyrimidylboronic acid conjugate

Characteristic $^1$H NMR (300 MHz, acetone-d6) peaks: δ ppm 7.85 (s, 2H), 5.25 (s, 1H, NH), 5.20 (s, 2H, NH), 1.40 (t, 6H).

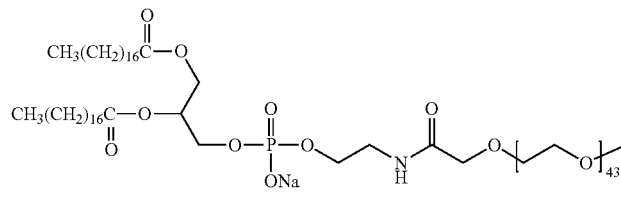

4-Aminocarbonylphenylboronic acid conjugate

Characteristic $^1$H NMR (300 MHz, acetone-d6) peaks: δ ppm 7.85 (d, 2H), 7.80 (d, 2H), 5.30 (s, 1H, NH), 5.25 (s, 2H, NH), 1.40 (t, 6H).

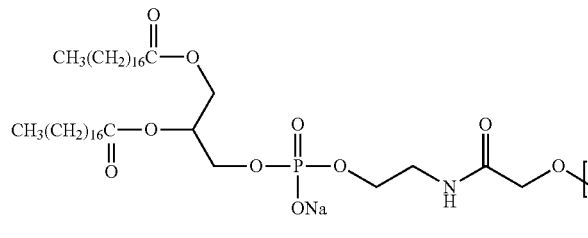

5-Amino-2,4-difluorophenylboronic acid

The insulin loading, extrusion, and purification processes were similar to that used for the sugar liposomes described above. The liposome had a mean diameter of 184±0.162 nm (suitable average liposome diameters may be from about 100 nm to about 300 nm). The encapsulated insulin was present in a concentration of approximately 15 mg/mL.

Preparation of Vesicle Compositions.

Two kinds of insulin loaded liposomal formulations, functionalized either with sugar molecules or boronic acid derivatives, were mixed and stirred at rt to form vesicle compositions. The mixtures were prepared using several mole ratios of sugar species to boronic acid species on the external surface of the liposomes, ranging from 1:2 to 1:50, to determine the excess of boronic acids required for vesicle composition formation. The pH of the mixture was also varied between 7 and 11, in order to select vesicle compositions that are formed at physiological pH.

TABLE 2

Example Conditions for Preparing Boronic Acid-Sugar Vesicle Compositions

| Boronic Acid Moiety | Sugar Liposome:Boronic Acid Liposome (v/v) | pH |
|---|---|---|
| 3-aminophenylboronic acid | 1:5 | 7.5 |
| 5-amino-2,4-difluorophenylboronic acid | 1:5 | 8 |
| 4-aminocarbonylphenylboronic acid | 1:20 | 8 |
| 3-fluoro-4-aminomethylphenylboronic acid | 1:10 | 8 |

Confirmation of Chemical Cross-Linkage of Boronic Acid and Sugar Moieties.

To confirm that the vesicle compositions were formed by chemical cross-linking of the boronic acid and sugar moieties, the agglomerates were exposed to 10 mM glucose. The

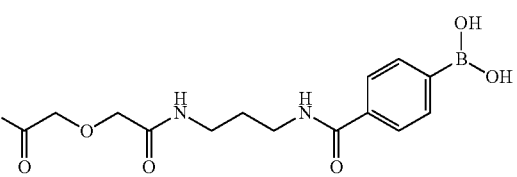

agglomerates were readily cleaved in the presence of glucose, due to competitive binding of the boronic acids with the free glucose. This was demonstrated by the increase in frequency of particles sized under 1 μm from 13% to 37% upon incubation with glucose.

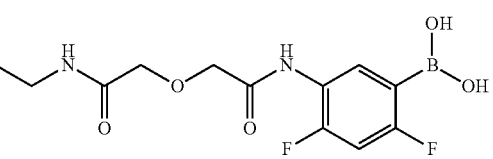

Example 6

In-Vitro Release of Insulin from the Boronate-Sugar Vesicle Compositions

A small volume (500 μL) of the agglomerates was loaded inside a tubular dialysis membrane (100,000 MWCO), sealed with clips, and dialyzed against a PBS solution (pH 7.4) for 30 min prior to cleaving with glucose to monitor the passive diffusion of insulin without trigger. This was followed by addition of glucose solution to the agglomerates inside the membrane at regular intervals to cleave the vesicle compositions and trigger the release of insulin. Aliquots were removed from the external phase every 15 min, and the insulin concentration was assayed by reading the absorbance at 214 nm. The assay was continued for several hours to verify a halt in release of encapsulated insulin.

Figure 9:
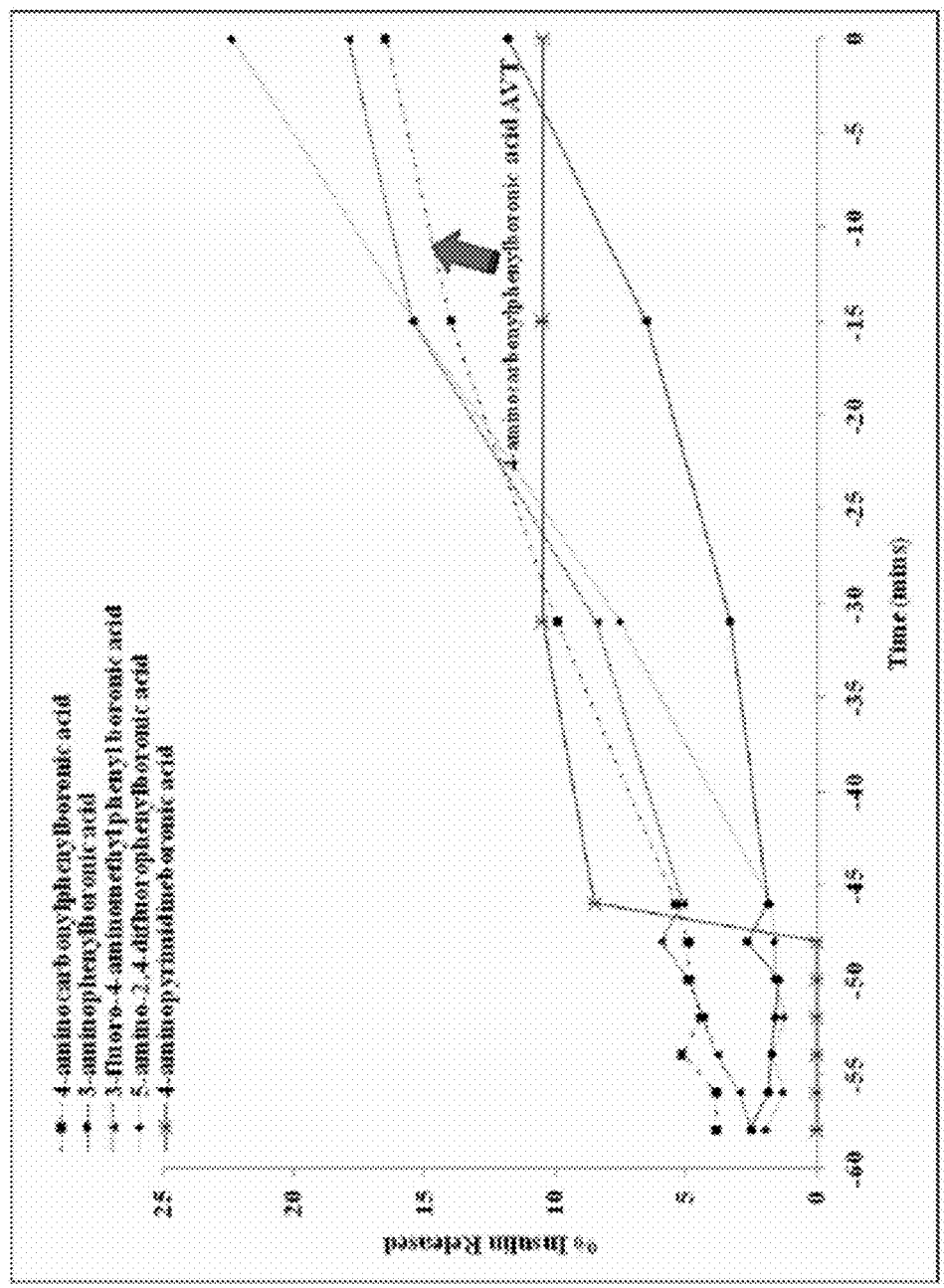
FIG. 9 illustrates cumulative release plots for four representative boronic acid-sugar vesicle compositions.

FIG. 9 illustrates cumulative release plots for four different boronate-glucose vesicle compositions, (4-aminocarbonylphenylboronic acid, 3-aminophenylboronic acid, 3-fluoro-4-aminoethylphenylboronic acid, and 5-amino-2,4-difluorophenylboronic acid), in the absence of glucose trigger. The 3-aminophenylboronic acid vesicle composition and the 4-aminocarbonylphenylboronic acid vesicle composition released 12% and 17% of their insulin content, respectively.

Insulin release from the 4-aminocarbonylphenylboronic acid vesicle composition upon addition of varying concentrations of glucose trigger was assayed for several hours. The trigger concentrations were chosen to mimic blood glucose levels at normoglycemic and hyperglycemic conditions. A control assay was also performed where the 4-aminocarbonylphenylboronic acid vesicle composition was triggered with PBS instead of glucose. The 4-aminocarbonylphenylboronic acid vesicle composition exhibited a burst release of insulin within two min after introduction of the glucose trigger. The release rate slows down over time until another dose of glucose is added, which triggered a new episode of burst release. In this example, the minimum concentration of glucose required for cleaving the 4-aminocarbonylphenylboronic acid vesicle composition and releasing insulin was 10 mmol/L, which corresponds to a blood glucose level of 180 mg/dL. No burst release of insulin was observed when the 4-aminocarbonylphenylboronic acid vesicle composition was triggered with glucose concentrations analogous to hypoglycemia (about 9 mg/dL) or normoglycemia (about 126 mg/dL), demonstrating that the example 4-aminocarbonylphenylboronic acid vesicle composition is suitable for maintaining normal blood glucose levels. Also, the insulin release rate from these vesicle compositions is dependent on the glucose concentration, thereby making the present embodiments useful in mitigating or avoiding hyper-insulinism.

Figure 10A:
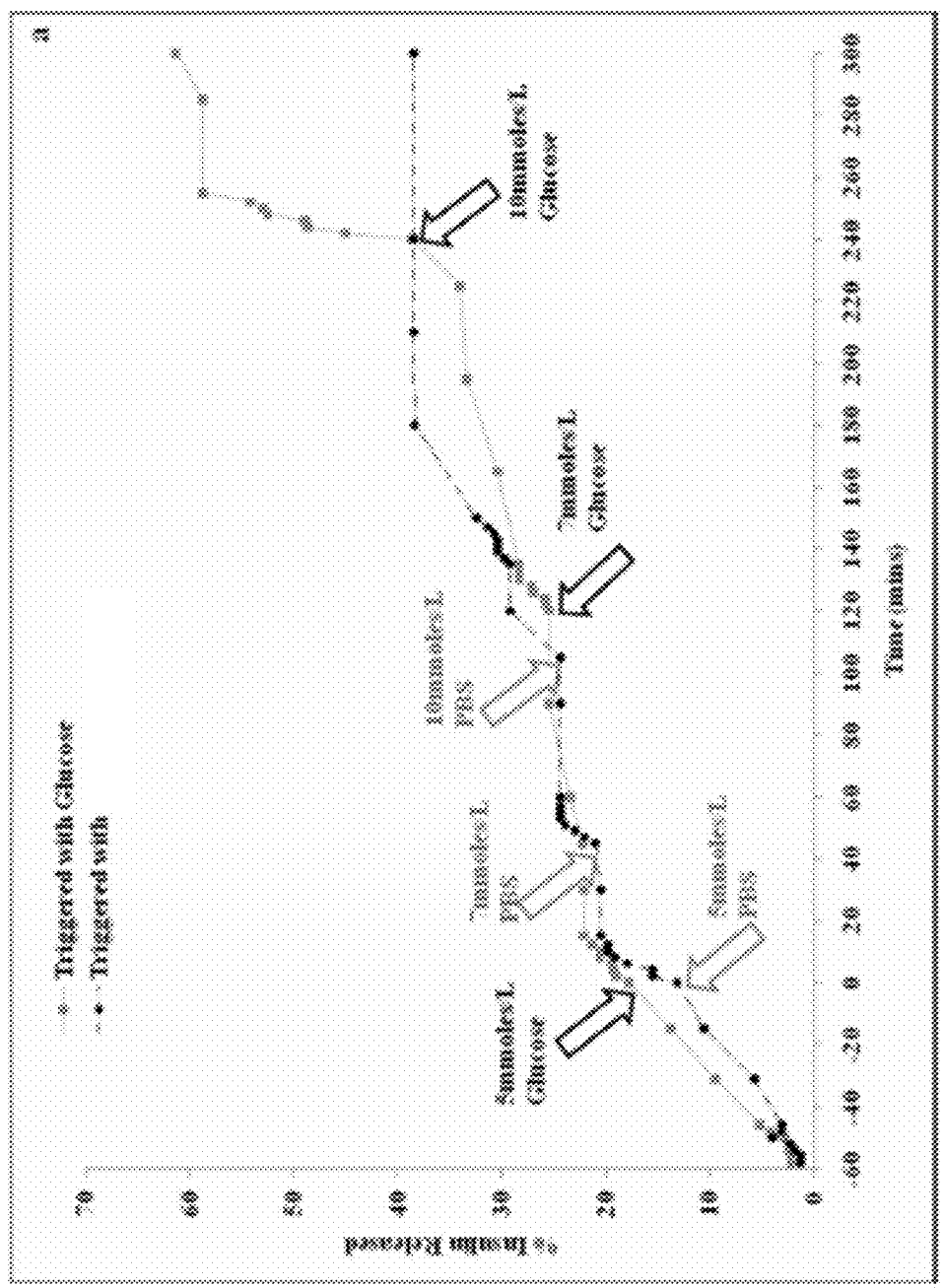
FIG. 10A illustrates cumulative plots for release of insulin from 4-aminocarbonylphenylboronic acid-sugar vesicle compositions triggered with 5 mM, 7 mM, and 10 mM glucose, as compared to triggering with 5 mM, 7 mM, and 10 mM PBS.
Figure 10B:
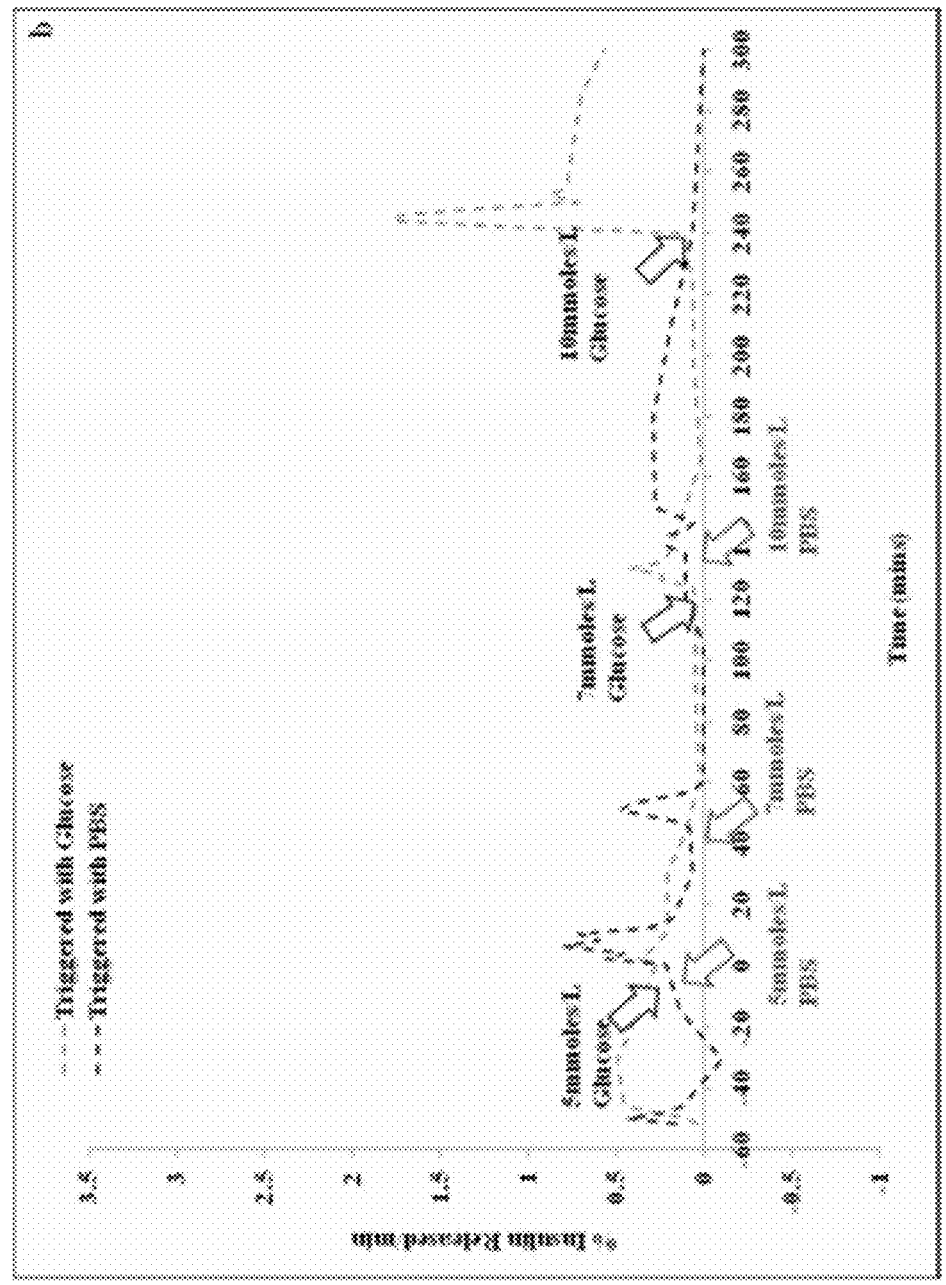
FIG. 10B illustrates differential plots for release of insulin from 4-aminocarbonylphenylboronic acid-sugar vesicle compositions triggered with 5 mM, 7 mM, and 10 mM glucose, as compared to triggering with 5 mM, 7 mM, and 10 mM PBS.

FIG. 10 illustrates (a) cumulative and (b) differential plots for release of insulin from 4-aminocarbonylphenylboronic acid vesicle compositions (4-aminocarbonylphenylboronic acid AVT) triggered with 5 mM, 7 mM, and 10 mM glucose, as compared to triggering with 5 mM, 7 mM, and 10 mM PBS.

Figure 11A:
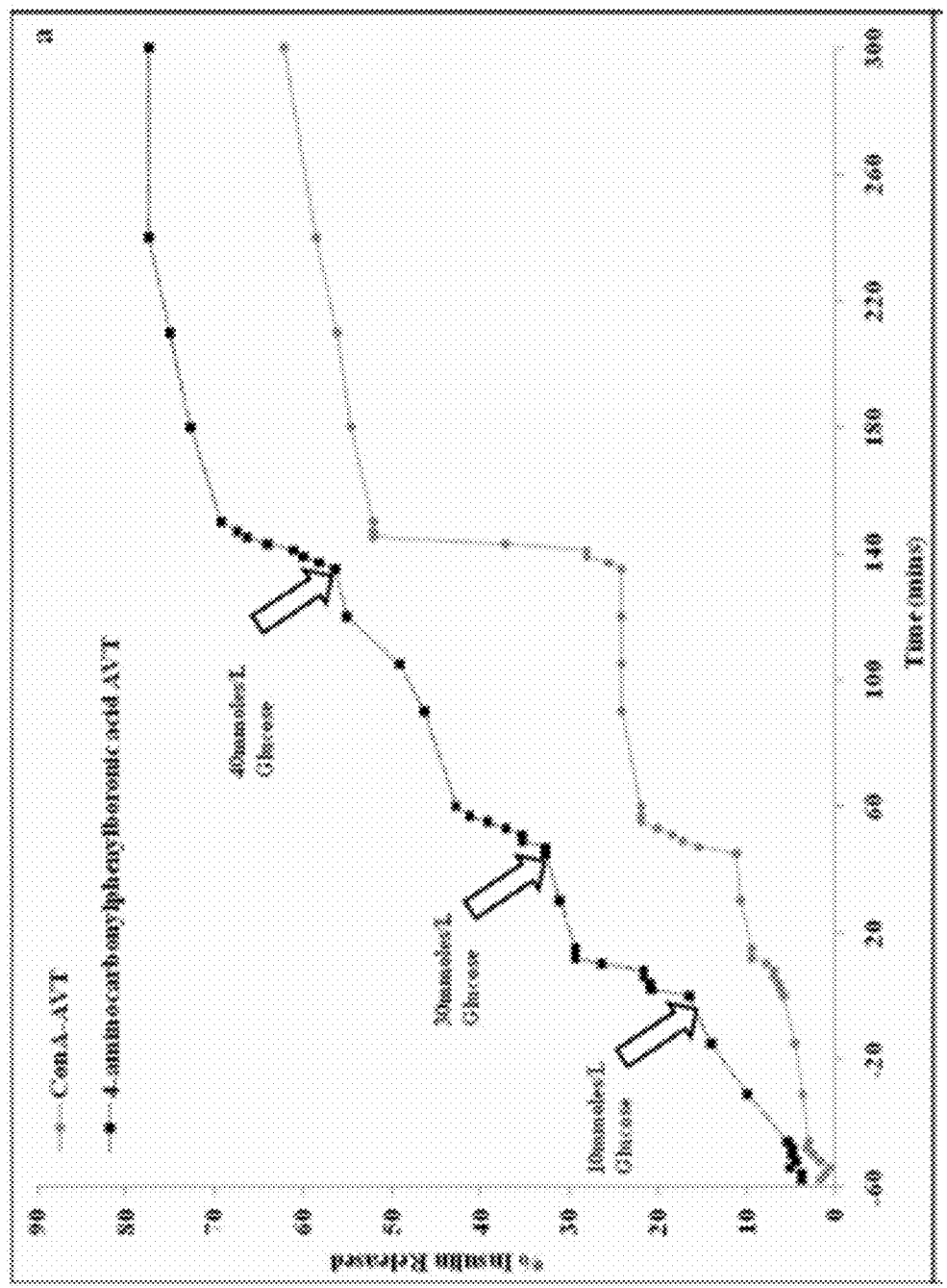
FIG. 11A illustrates cumulative plots for release of insulin from 4-aminocarbonylphenylboronic acid-sugar vesicle compositions ("4-aminocarbonylphenylboronic acid AVT") and Concanavalin A vesicle compositions ("ConA-AVT") triggered with 10 mM, 30 mM, and 40 mM glucose.
Figure 11B:
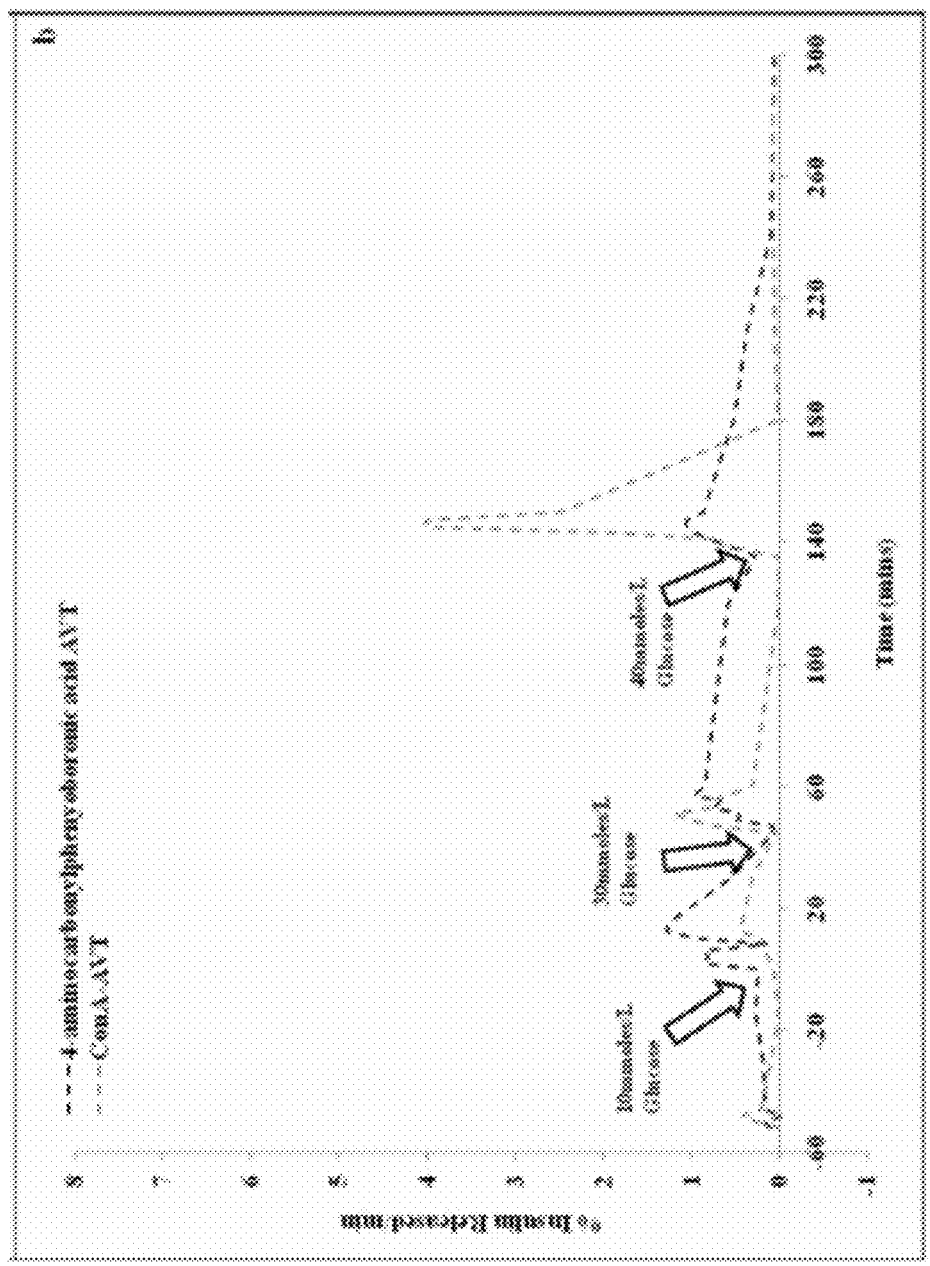
FIG. 11B illustrates differential plots for release of insulin from 4-aminocarbonylphenylboronic acid-sugar vesicle compositions ("4-aminocarbonylphenylboronic acid AVT") and Concanavalin A vesicle compositions ("ConA-AVT") triggered with 10 mM, 30 mM, and 40 mM glucose.

FIG. 11 illustrates (a) cumulative and (b) differential plots for release of insulin from 4-aminocarbonylphenylboronic acid and ConA vesicle compositions triggered with 10 mM, 30 mM, and 40 mM glucose.

Those skilled in the art will appreciate that numerous changes and modifications can be made to the embodiments disclosed herein, and that such changes and modifications can be made without departing from the spirit of the invention. It is, therefore, intended that the appended claims cover all such equivalent variations as fall within the true spirit and scope of the invention.

What is claimed is:

1. A vesicle composition, comprising:

(A) a first liposome composition, comprising:

(1) a first phospholipid;

(2) cholesterol; and (3) a phospholipid-polyethylene glycol-boronic acid derivative conjugate, comprising:

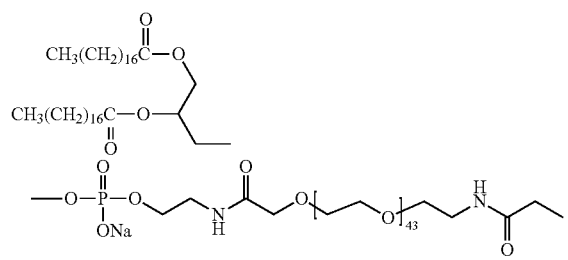

-continued

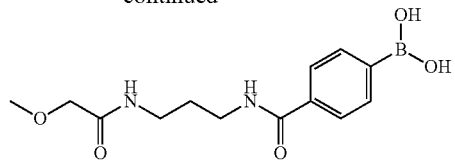

wherein n=30-60, and wherein the first liposome composition encapsulates a first therapeutic compound; and (B) a second liposome composition, comprising:

(1) a second phospholipid;

(2) cholesterol; and (3) a phospholipid-polyethylene glycol-glycosyl conjugate comprising a glycosyl moiety comprising a glucosyl moiety, a galactosyl moiety, or a mannopyranosidyl moiety, wherein:

the second liposome composition encapsulates a second therapeutic compound; and the first liposome composition is cross-linked to the second liposome composition.

2. The vesicle composition of claim 1, wherein the glycosyl moiety comprises the glucosyl moiety.

3. The vesicle composition of claim 1, wherein the glycosyl moiety comprises the galactosyl moiety.

4. The vesicle composition of claim 1, wherein the glycosyl moiety comprises the mannopyranosidyl moiety.

5. The vesicle composition of claim 1, wherein the first therapeutic compound and the second therapeutic compound each comprises insulin.

6. The vesicle composition of claim 1, wherein at least one of the first and the second liposome composition releases an amount of its respective therapeutic compound in response to a presence of a sugar.

7. The vesicle composition of claim 6, wherein the amount of respective therapeutic compound released is dependent upon a concentration of the sugar.

8. The vesicle composition of claim 1, wherein the first therapeutic compound and the second therapeutic compound are the same.

9. A vesicle composition useful in the treatment of diabetes, comprising:

(A) a first liposome composition, comprising:

(1) a first phospholipid;

(2) cholesterol; and (3) a phospholipid-polyethylene glycol-boronic acid derivative conjugate, comprising a boronic acid derivative moiety that is less cytotoxic and/or less inflammatory than the boronic acid derivative moiety in its free form, comprising:

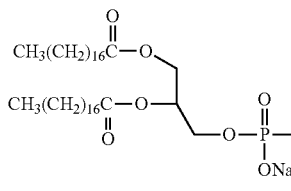

wherein n=30-60, and
wherein the first liposome composition encapsulates insulin; and
(B) a second liposome composition, comprising:
(1) a second phospholipid;
(2) cholesterol; and
(3) a phospholipid-polyethylene glycol-glycosyl conjugate comprising a glycosyl moiety comprising a glucosyl moiety, a galactosyl moiety, or a mannopyranosidyl moiety,
wherein:
the second liposome composition encapsulates insulin; and
the first liposome composition is cross-linked to the second liposome composition.

10. The vesicle composition of claim 9, wherein the boronic acid derivative moiety of the phospholipid-polyethylene glycol-boronic acid derivative conjugate and the glycosyl moiety of the phospholipid-polyethylene glycol-glycosyl conjugate are covalently bonded to each other.

11. A vesicle composition capable of being injected into a patient, comprising:
(A) a first liposome, comprising:
(1) DPPC;
(2) cholesterol; and
(3) a DSPE-PEG-boronic acid derivative conjugate, comprising:

(1) 40-70 mole % DPPC;
(2) 20-50 mole % cholesterol; and
(3) 1-15 mole % DSPE-PEG-boronic acid derivative conjugate.

13. The vesicle composition of claim 11, wherein the first liposome comprises:
(1) about 56.4 mole % DPPC;
(2) about 40 mole % cholesterol; and
(3) about 3.6 mole % DSPE-PEG-boronic acid derivative conjugate.

14. The vesicle composition of claim 11, wherein the second liposome comprises:
(1) 40-70 mole % DPPC;
(2) 20-50 mole % cholesterol;
(3) 1-15 mole % DSPE-PEG-glucosyl conjugate;
(4) 1-15 mole % DSPE-PEG-galactosyl conjugate; and
(5) 1-15 mole % DSPE-PEG-mannopyranosidyl conjugate.

15. The vesicle composition of claim 11, wherein the second liposome comprises:
(1) about 56.4 mole % DPPC;
(2) about 40 mole % cholesterol;
(3) about 1.2 mole % DSPE-PEG-glucosyl conjugate;
(4) about 1.2 mole % DSPE-PEG-galactosyl conjugate; and

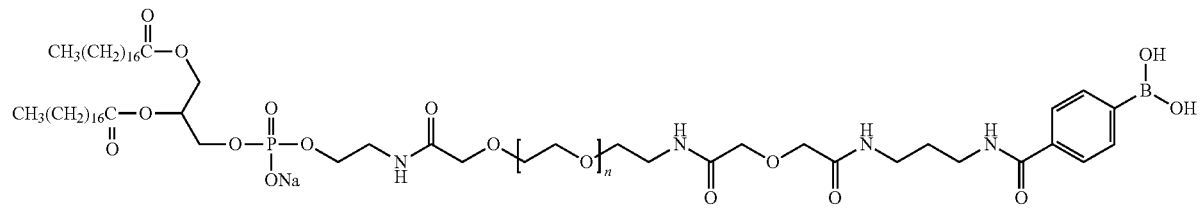

wherein n=30-60, and
wherein the first liposome encapsulates insulin; and
(B) a second liposome, comprising:
(1) DPPC;
(2) cholesterol;
(3) a DSPE-PEG-glucosyl conjugate;
(4) a DSPE-PEG-galactosyl conjugate; and
(5) a DSPE-PEG-mannopyranosidyl conjugate,
wherein:
the second liposome encapsulates insulin; and
the first liposome is cross-linked to the second liposome.

12. The vesicle composition of claim 11, wherein the first liposome comprises:

(5) about 1.2 mole % DSPE-PEG-mannopyranosidyl conjugate.

16. The vesicle composition of claim 11, wherein a molecule of the DSPE-PEG-boronic acid derivative conjugate of the first liposome is covalently bonded to at least one of a molecule of the DSPE-PEG-glucosyl conjugate, the DSPE-PEG-galactosyl conjugate, and the DSPE-PEG-mannopyranosidyl conjugate of the second liposome.

17. The vesicle composition of claim 11, wherein at least one of the first and the second liposomes releases an amount of insulin in response to a presence of glucose.

* * * * *